US008058248B2

(12) United States Patent
Grubman et al.

(10) Patent No.: US 8,058,248 B2
(45) Date of Patent: Nov. 15, 2011

(54) FOOT AND MOUTH DISEASE VIRUS VACCINE COMPRISING INTERFERONS

(75) Inventors: Marvin J. Grubman, Southold, NY (US); Jarasvech Chinsangaram, Beverly, MA (US); Marla Koster, Cutchogue, NY (US); Mauro P. Moraes, Vicosa (BR)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/128,463

(22) Filed: Apr. 24, 2002

(65) Prior Publication Data
US 2003/0171314 A1    Sep. 11, 2003

Related U.S. Application Data

(60) Provisional application No. 60/286,345, filed on Apr. 26, 2001.

(51) Int. Cl.
*A61K 48/00* (2006.01)
*A01N 63/00* (2006.01)
*C07H 19/00* (2006.01)
*C07H 21/00* (2006.01)
*C07H 21/02* (2006.01)

(52) U.S. Cl. .................... 514/44 R; 424/93.2; 536/23.1; 536/23.52

(58) Field of Classification Search ................. 536/23.1, 536/23.52; 514/44; 424/93.1; 435/455, 435/320.1
See application file for complete search history.

(56) References Cited

U.S. PATENT DOCUMENTS

| | | | |
|---|---|---|---|
| 4,795,436 A | | 1/1989 | Robinson |
| 5,612,040 A | * | 3/1997 | Mason et al. ............. 424/205.1 |
| 5,672,510 A | | 9/1997 | Eglitis et al. |
| 5,739,118 A | | 4/1998 | Carrano et al. |
| 5,814,482 A | | 9/1998 | Dubensky, Jr. et al. |
| 5,824,316 A | * | 10/1998 | Grubman et al. ........... 424/216.1 |
| 5,831,023 A | | 11/1998 | Capon et al. |
| 6,045,802 A | | 4/2000 | Schlom et al. |
| 6,066,624 A | * | 5/2000 | Woo et al. ........................ 514/44 |
| 6,221,361 B1 | | 4/2001 | Cochran et al. |
| 6,544,780 B1 | | 4/2003 | Wang |

OTHER PUBLICATIONS

Ahmed, et al. (1999) Hum. Gene Therapy 10(1): 77-84.*
Knipe, et al. (2001) Fundamental Virol., 4th Ed., Lippincott, Williams & Wilkins, Philadelphia, PA, pp. 534, 1091.*
Gorecki (2001) Expert Opin. Emerg. Drugs 6(2): 187-98.*
Verma, et al. (1997) Nature 398:239-42.*
Eck, et al. (1996) The Pharmacological Basis of Therapeutics, 9th Ed., by McGraw-Hill, NY. pp. 77-101.*
Nakano, et al. (1997) J. Virol. 71(9): 7101-09.*
Torres, et al. (1995) Virology, 213: 503-516.*
Hammond, et al. (2001) Vaccine, 19: 3752-58.*
Shi, et al. (2001) J. Virology, 75(23): 11474-82.*
Pettersson, et al. (2000) Laboratory Investigation, 80(1): 99-115.*
Mittal, et al. (1996) Virology, 222: 299-309.*
Raz, et al. (1994) Proc. Natl. Acad. Sci., USA., 91: 9519-23.*
Weiss, et al. (2000) Infection and Immunity, 68(10): 5914-19.*
van Rooij, et al. (1998) Vet. Immunol. Immunopath., 66: 113-26.*
Muller, et al. (1998) J. Virol., 72(1): 20-31.*
Dufour, et al. (2000) J. Interferon and Cytokine Research, 20: 889-895.*
Cunliffe, et al. (1997) Can. J. Comp. Med., 41: 117-121.*
Konishi, et al. (2000) Virology, 268: 49-55.*
Moraes, M. P. et al., "Early protection against homologous challenge after a single dose of replication-defective human adenovirus type 5 expressing capsid proteins of foot-and-mouth disease virus (FMDV) strain A24", *Vaccine*, vol. 20, pp. 1631-1639, 2002.
Moraes, M. P. et al., "pAd5-Blue: Direct Ligation System for Engineering Recombinant Adenovirus Constructs", *BioTechniques*, vol. 31, (5), pp. 1-4, Nov. 2001.
Mayr, G. et al., "Immune responses and protection against foot-and-mouth disease virus (FMDV) challenge in swine vaccinated with adenovirus-FMDV constructs", *Vaccine*, vol. 19, pp. 2152-2162, 2001.
Mayr, G. et al., "Development of Replication-Defective Adenovirus Serotype 5 Containing the Capsid and 3C Protease Coding Regions of Foot-and-Mouth Disease Virus as a Vaccine Candidate", *Virology*, vol. 263, pp. 496-506, 1999.
Vilcek, J. et al., "Interferons and Other Cytokines", *Virology*, Chapter 13, pp. 375-399, 1996.
Chinsangaram, J. et al., "Inhibition of L-Deleted Foot-and-Mouth Disease Virus Replication by Alpha/Beta Interferon Involves Double-Stranded RNA-Dependent Protein Kinase", *Journal of Virology*, vol. 75, (12), pp. 000-000, Jun. 2001.
Chinsangaram, J. et al., "Ability of Foot-and-Mouth Disease Virus to Form Plaques in Cell Culture Is Associated with Suppression of Alpha/Beta Interferon", *Journal of Virology*, vol. 73, pp. 9891-9898, 1999.

* cited by examiner

*Primary Examiner* — Robert M Kelly
(74) *Attorney, Agent, or Firm* — John D. Fado; Evelyn M. Rabin

(57) ABSTRACT

Early protection of susceptible animals against foot and mouth disease (FMD) may be achieved by inoculating the animals with a vaccine comprising an interferon DNA sequence. One day after inoculation, animals have been found protected from challenge with virulent foot and mouth disease virus. Co-administration with an effective foot and mouth disease virus vaccine provides protection prior to the development of specific immunity, a feature especially desireable during a FMD outbreak.

19 Claims, 26 Drawing Sheets

ATGGCCCCAACCTCAGCCTTTCTCACGGCCCTGGTGCTGCTCAGCTGCAAG
GCCATCTGCTCTCTGGGCTGCGACCTGCCTCAGACCCACAGCCTGGCTCAC
ACCAGGGCCCTGAGGCTCCTGGCACAAATGAGGAGAATCTCCCCCTTCTCC
TGCCTGGACCACAGAAGGGACTTTGGGTTCCCCCAAGAGGCCTTGGGGGG
CAACCAGGTCCAGAAGGCTCAAGCCATGGCTCTGGTGCATGAGATGCTCCA
GCAGACCTTCCAGCTCTTCAGCACAGAGGGCTCGGCTGCTGCCTGGAATGA
GAGCCTCCTGCACCAGTTCTGCACTGGACTGGATCAGCAGCTCAGGGACCT
GGAAGCCTGTGTCATGCAGGAGGTGGGGCTGGAAGGGACGCCCCTGCTG
GAGGAGGACTCCATCCTGGCTGTGAGGAAATACTTCCACAGACTCACCCTC
TATCTGCAAGAGAAGAGCTACAGCCCTGTGCCTGGGAGATCGTCAGGGCA
GAAGTCATGAGAGCCTTCTCTTCCTCCAGAAACCTGCAAGACAGACTGAGG
AAGAAGGAGTGAGGATCCATCC

FIG. 1A

ATGGCCCCAACCTCAGCCTTCCTCACGGCCCTGGTGCTACTCAGCTGCAAT
GCCATCTGCTCTCTGGGCTGTGACCTGCCTCAGACCCACAGCCTGGCTCAC
ACCAGGGCCCTGAGGCTCCTGGCACAAATGAGGAGAATCTCTCCCTTCTCC
TGCCTGGACCACAGAAGGGACTTTGGATCCCCTCATGAGGCTTTGGGGGC
AACCAGGTCCAGAAGGCTCAAGCCATGGCTCTGGTGCATGAGATGCTCCAG
CAGACCTTCCAGCTCTTCAGCACAGAGGGCTCGGCTGCTGCCTGGAATGAG
AGCCTCCTGCACCAGTTCTGCACTGGACTGGATCAGCAGCTCAGGGACCTG
GAAGCCTGTGTCATGCAGGAGGCGGGGCTGGAAGGGACCCCCTGCTGGA
GGAGGACTCCATCCTGGCTGTGAGGAAATACTTCCACAGACTCACCCTCTA
TCTGCAAGAGAAGAGCTACAGCCCTGTGCCTGGGAGATCGTCAGGGCAG
AAGTCATGAGATCCTTCTCTTCCTCCAGAAACCTGCAAGACAGACTGAGGAA
GAAGGAGTGAGGATCCATCC

FIG. 1B

```
ATGGCTAACAAGTGCATCCTCCAAATCGCTCTCCTGATGTGTTTCTCCACCA
CAGCTCTTTCCATGAGCTATGATGTGCTTCGATACCAACAAAGGAGCAGCAA
TTTGGCATGTCAGAAGCTCCTGGGACAGTTGCCTGGGACTCCTCAATATTG
CCTCGAAGATAGGATGAACTTTGAGGTCCCTGAGGAGATTATGCAACCACC
ACAATTCCAGAAGGAAGATGCAGTATTGATTATCCACGAGATGCTCCAGCAG
ATCTTCGGCATTCTCAGAAGAAATTTCTAGCACTGGCTGGAATGAAACCG
TCATTAAGACTATCCTTGTGGAACTTGATGGGCAGATGGATGACCTGGAGA
CAATCCTGGAGGAAATCATGGAGGAGGAAAATTTCCCCAGGGGAGACATGA
CCATTCTTCACCTGAAGAAATATTACTTGAGCATTCTGCAGTACCTGAAGTC
CAAGGAGTACAGAAGCTGTGCCTGGACAGTCGTCCAAGTGGAAATCCTCAG
GAACTTTTCTTTCCTTAACAGACTTACAGATTACCTCCGGAACTGAGGATCC
ATCC
```

FIG. 2

```
ATGGCCCCAGCCTGGTCCTTACTCCTGGCCCTGCTGCTGCTCAGCTGCAAC
GCCATCTGCTCTCTGGGCTGCCACCTGCCTCACACCCACAGCCTGCCCAAC
AGGAGGGTCCTGATGCTCCTGAGACAACTGAGGAGGGTCTCCCCTTCCTCC
TGCCTGCAGGACAGAAATGACTTCGCATTCCCCCAGGAGGCGCTGGGTGG
CAGCCAGTTGCAGAAGGCTCAAGCCATCTCTGTGCTCCACGAGGTGACCCA
GCACACCTTCCAGCTTTTCAGCACAGAGGGCTCGGCCGCTGTGTGGGACAA
GAGCCTCCTGGACAAGCTCCATGCTGCACTGGATCAGCAGCTCACTGACCT
GCAAGCCTGTCTGAGGCAGGAGGAGGGGCTGCGAGGGGCTCCCCTACTCA
ACGAGGACTCCAGCCTGGCTGTGAGGAAATACTTCCACAGACTCACTGTCT
ATCTGCAAGAGAAGAGACACAGCCCTTGTGCCTGGGAGGTTGTCAGAGCAC
AAATCATGAGAGCCTTCTCTTCCTCAACCAACTTGCAGGAGAGTTTCAGGAG
AAAGGACTGAGGATCCATCC
```

FIG. 3

```
ATGACCCACCGGTGCCTCCTCCCGATGGTTCTCCTGCTGTGTTTCTCCACC
ACAGCTCTTTCCAGGAGCTACAGCTTGCTTCGATTCCAACAACGTCAGAGC
CTTAAAGAGTGTCAGAAACTCCTGGGGCAGTTACCTTCAACTTCTCAACATT
GCCTCGAGGCCAGGATGGACTTCCAGATGCCTGAGGAGATGAAGCAAGAA
CAGCAGTTCCAGAAGGAAGATGCCATATTGGTCATGTATGAGATGCTCCAG
CACATCTTCGGCATTCTCACCAGAGACTTCTCCAGCACTGGCTGGTCTGAG
ACCATCATCGAGGACCTCCTTGAGGAACTCTATGGGCAGATGAATCGTCTG
CAGCCAATCCAGAAGGAAATAATGCAGAAGCAAAACTCCACTACGGGAGAC
ATGATCGTTCCCCACCTAGGGAAATATTACTTCAACCTCATGCAGTACCTGG
AGTCCAAGGAGTACGACAGGTGTGCCTGGACAGTCGTGCAAGTGCAAATAC
TCACGAACGTTTCTTTCCTGATGAGACTAACAGCTTCCCTCCGTGACTGAGG
ATCCATCC
```

FIG. 4

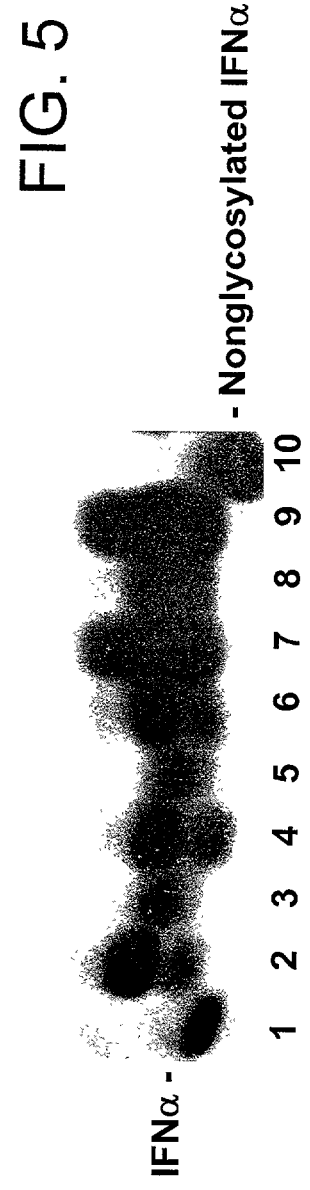

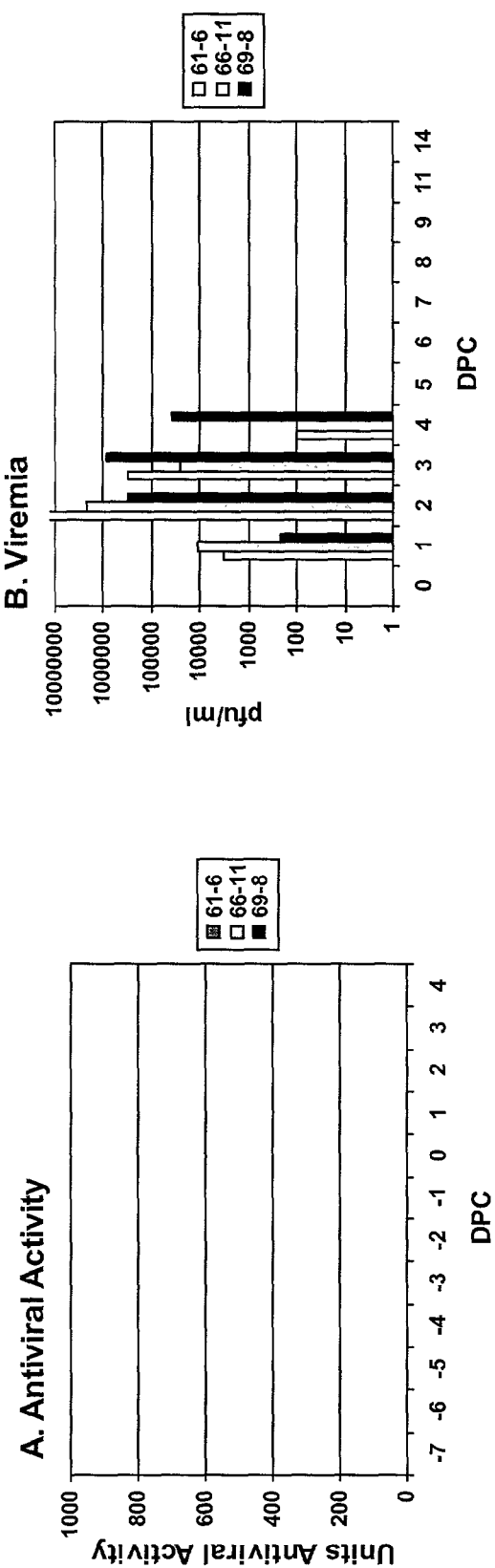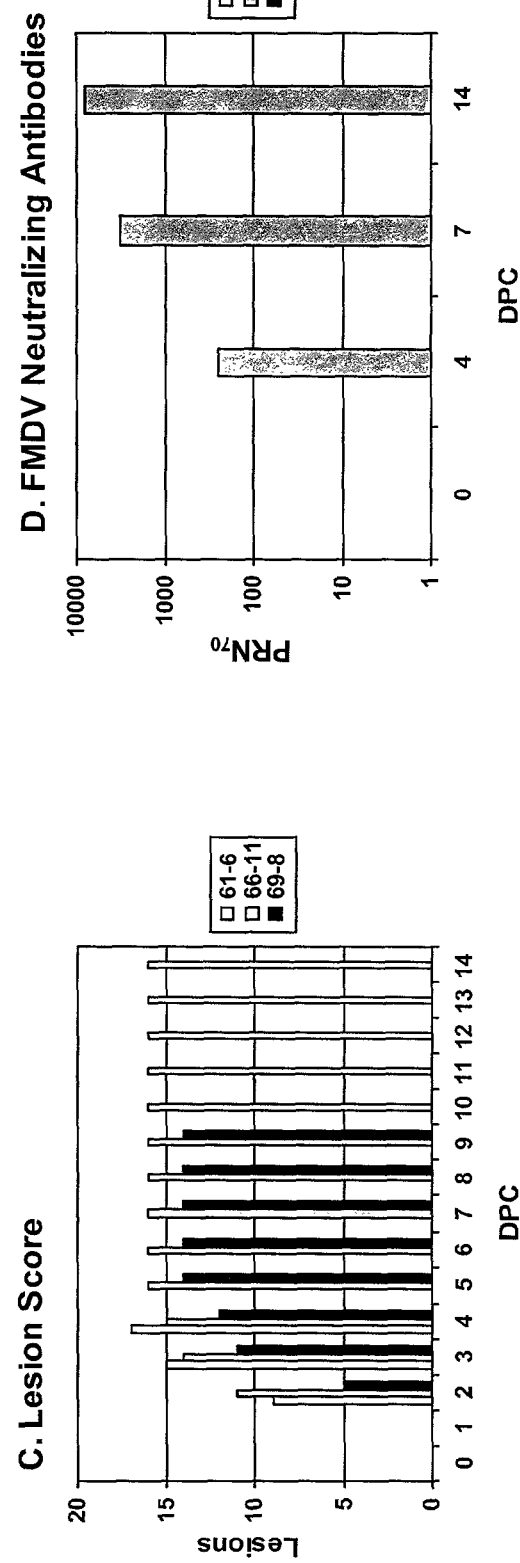
FIG. 14

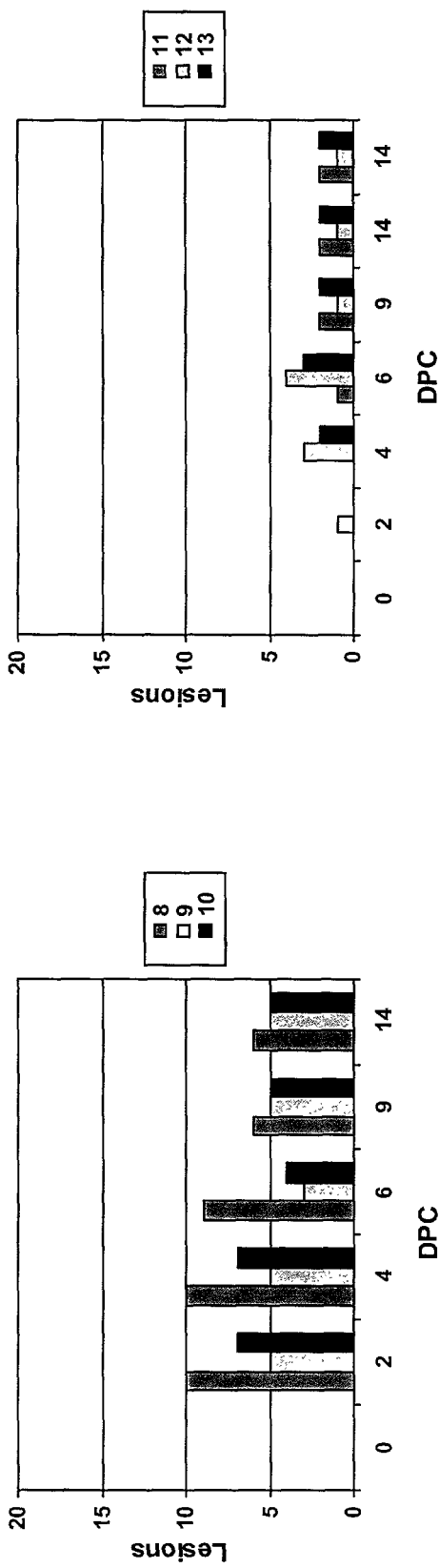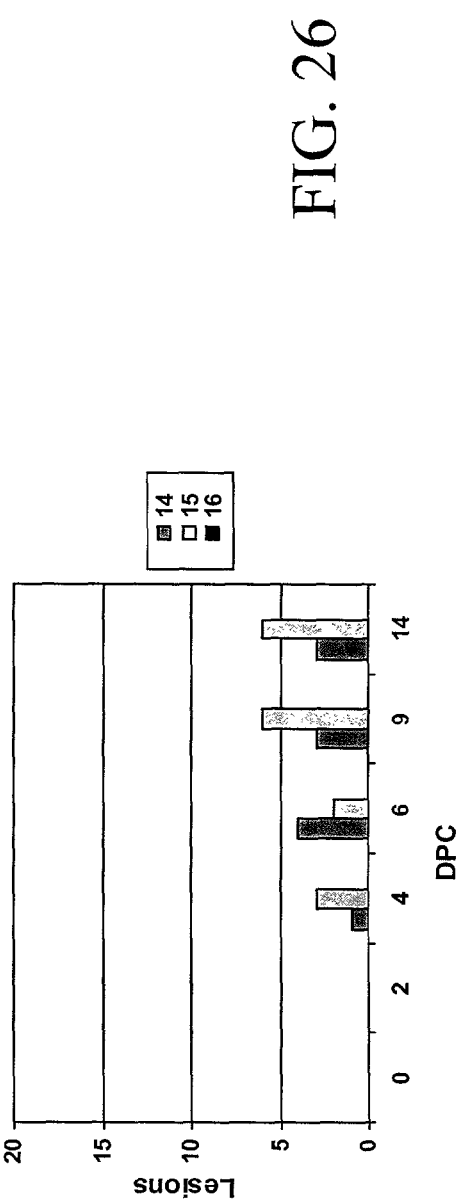
FIG. 26

SEQUENCE LISTING

<160> NUMBER OF SEQ ID NOS: 13

<210> SEQ ID NO 1
<211> LENGTH: 580
<212> TYPE: DNA
<213> ORGANISM: Porcine

<400> SEQUENCE: 1

```
atggccccaa cctcagcctt tctcacggcc ctggtgctgc tcagctgcaa ggccatctgc      60
tctctgggct gcgacctgcc tcagacccac agcctggctc acaccagggc cctgaggctc     120
ctggcacaaa tgaggagaat ctccccttc tcctgcctgg accacagaag ggactttggg     180
ttcccccaag aggccttggg gggcaaccag gtccagaagg ctcaagccat ggctctggtg     240
catgagatgc tccagcagac cttccagctc ttcagcacag agggctcggc tgctgcctgg     300
aatgagagcc tcctgcacca gttctgcact ggactggatc agcagctcag ggacctggaa     360
```

```
gcctgtgtca tgcaggaggt ggggctggaa gggacgcccc tgctggagga ggactccatc    420
ctggctgtga ggaaatactt ccacagactc accctctatc tgcaagagaa gagctacagc    480
ccctgtgcct gggagatcgt cagggcagaa gtcatgagag ccttctcttc ctccagaaac    540
ctgcaagaca gactgaggaa gaaggagtga ggatccatcc                          580

<210> SEQ ID NO 2
<211> LENGTH: 580
<212> TYPE: DNA
<213> ORGANISM: Porcine

<400> SEQUENCE: 2
atggccccaa cctcagcctt cctcacggcc ctggtgctac tcagctgcaa tgccatctgc     60
tctctgggct gtgacctgcc tcagacccac agcctggctc acaccagggc cctgaggctc    120
ctggcacaaa tgaggagaat ctctcccttc cctgcctgg accacagaag ggactttgga    180
tcccctcatg aggcttttgg gggcaaccag gtccagaagg ctcaagccat ggctctggtg    240
catgagatgc tccagcagac cttccagctc ttcagcacag agggctcggc tgctgcctgg    300
aatgagagcc tcctgcacca gttctgcact ggactggatc agcagctcag ggacctggaa    360
gcctgtgtca tgcaggaggc ggggctggaa gggaccccc tgctggagga ggactccatc     420
ctggctgtga ggaaatactt ccacagactc accctctatc tgcaagagaa gagctacagc    480
ccctgtgcct gggagatcgt cagggcagaa gtcatgagat ccttctcttc ctccagaaac    540
ctgcaagaca gactgaggaa gaaggagtga ggatccatcc                          580

<210> SEQ ID NO 3
<211> LENGTH: 571
<212> TYPE: DNA
<213> ORGANISM: Porcine

<400> SEQUENCE: 3
atggctaaca agtgcatcct ccaaatcgct ctcctgatgt gtttctccac cacagctctt     60
tccatgagct atgatgtgct tcgataccaa caaaggagca gcaatttggc atgtcagaag    120
ctcctgggac agttgcctgg gactcctcaa tattgcctcg aagataggat gaactttgag    180
gtccctgagg agattatgca accaccacaa ttccagaagg aagatgcagt attgattatc    240
cacgagatgc tccagcagat cttcggcatt tcagaagaa atttctctag cactggctgg    300
aatgaaaccg tcattaagac tatccttgtg gaacttgatg ggcagatgga tgacctggag    360
acaatcctgg aggaaatcat ggaggaggaa aatttcccca ggggagacat gaccattctt    420
cacctgaaga aatattactt gagcattctg cagtacctga gtccaaggga gtacagaagc    480
tgtgcctgga cagtcgtcca agtggaaatc tcaggaact tttctttcct taacagactt    540
acagattacc tccggaactg aggatccatc c                                   571

<210> SEQ ID NO 4
<211> LENGTH: 580
<212> TYPE: DNA
<213> ORGANISM: Bovine

<400> SEQUENCE: 4
atggccccag cctggtcctt actcctggcc ctgctgctgc tcagctgcaa cgccatctgc     60
tctctgggct gccacctgcc tcacacccac agcctgccca acaggagggt cctgatgctc    120
ctgagacaac tgaggagggt ctccccttcc tcctgcctgc aggacagaaa tgacttcgca    180 ttccccagg aggcgctggg tgcagccag ttgcagaagg ctcaagccat ctctgtgctc    240
```

```
cacgaggtga cccagcacac cttccagctt ttcagcacag agggctcggc cgctgtgtgg    300
gacaagagcc tcctggacaa gctccatgct gcactggatc agcagctcac tgacctgcaa    360
gcctgtctga ggcaggagga ggggctgcga ggggctcccc tactcaacga ggactccagc    420
ctggctgtga ggaaatactt ccacagactc actgtctatc tgcaagagaa gagacacagc    480
ccttgtgcct gggaggttgt cagagcacaa atcatgagag ccttctcttc ctcaaccaac    540
ttgcaggaga gtttcaggag aaaggactga ggatccatcc                          580

<210> SEQ ID NO 5
<211> LENGTH: 571
<212> TYPE: DNA
<213> ORGANISM: Bovine

<400> SEQUENCE: 5
atgacccacc ggtgcctcct cccgatggtt ctcctgctgt gtttctccac cacagctctt     60
tccaggagct acagcttgct tcgattccaa caacgtcaga gccttaaaga gtgtcagaaa    120
ctcctggggc agttaccttc aacttctcaa cattgcctcg aggccaggat ggacttccag    180
atgcctgagg agatgaagca agaacagcag ttccagaagg aagatgccat attggtcatg    240
tatgagatgc tccagcacat cttcggcatt ctcaccagag acttctccag cactggctgg    300
tctgagacca tcatcgagga cctccttgag gaactctatg gcagatgaa tcgtctgcag     360 ccaatccaga aggaaataat gcagaagcaa aactccacta cgggagacat gatcgttccc    420
cacctaggga aatattactt caacctcatg cagtacctgg agtccaagga gtacgacagg    480
tgtgcctgga cagtcgtgca agtgcaaata ctcacgaacg tttctttcct gatgagacta    540
acagcttccc tccgtgactg aggatccatc c                                   571

<210> SEQ ID NO 6
<211> LENGTH: 21
<212> TYPE: DNA
<213> ORGANISM: Bovine

<400> SEQUENCE: 6
ccgatggccc cagcctggtc c                                               21

<210> SEQ ID NO 7
<211> LENGTH: 34
<212> TYPE: DNA
<213> ORGANISM: Porcine

<400> SEQUENCE: 7
ggatggatcc tcagtccttt ctcctgaawy tctc                                 34

<210> SEQ ID NO 8
<211> LENGTH: 26
<212> TYPE: DNA
<213> ORGANISM: Porcine

<400> SEQUENCE: 8
catcatgacc yaccggtgcc tcctcc                                          26

<210> SEQ ID NO 9
<211> LENGTH: 34
<212> TYPE: DNA
<213> ORGANISM: Porcine

<400> SEQUENCE: 9
ggatggatcc tcaktcacgg asgkaacctg ttag                                 34
```

```
<210> SEQ ID NO 10
<211> LENGTH: 18
<212> TYPE: DNA
<213> ORGANISM: Porcine

<400> SEQUENCE: 10 atggcccccaa cctcagcc                                              18

<210> SEQ ID NO 11
<211> LENGTH: 31
<212> TYPE: DNA
<213> ORGANISM: Porcine

<400> SEQUENCE: 11
tggatcctca ctccttcttc ctcagtctgt c                                31

<210> SEQ ID NO 12
<211> LENGTH: 21
<212> TYPE: DNA
<213> ORGANISM: Porcine

<400> SEQUENCE: 12
atggctaaca agtgcatcct c                                           21

<210> SEQ ID NO 13
<211> LENGTH: 34
<212> TYPE: DNA
<213> ORGANISM: Porcine

<400> SEQUENCE: 13
ggatggatcc tcagttccgg aggtaatctg taag                             34
```

FOOT AND MOUTH DISEASE VIRUS VACCINE COMPRISING INTERFERONS

This application claims the benefit of U.S. Provisional Application No. 60/286,345, filed Apr. 26, 2001, which is incorporated herein by reference in its entirety.

BACKGROUND OF THE INVENTION

1. Field of the Invention

Foot-and-mouth disease (FMD) is economically one of the most important animal diseases of livestock worldwide. The disease is caused by the foot-and-mouth disease virus (FMDV) and is highly infectious, spreading rapidly by contact or aerosol.

Because of the highly infectious nature of FMD, countries free of the disease maintain rigid quarantine and import restrictions on animals and animal products from infected countries in order to prevent its introduction and to allow continued active participation in international trade. The disease does not occur in the U.S., Canada or Mexico, and its continued absence from North America is a priority for the U.S. livestock industry and the United States Department of Agriculture (USDA).

Inactivated whole virus vaccines are conventionally used in FMD control programs and have been largely successful in controlling the disease. Problems associated with the current vaccines, however, include a requirement for high-containment facilities to produce the virus needed for vaccine manufacture in, the occurrence antigenic variation of the virus resulting in numerous virus serotypes and subtypes, and the inability of vaccines to rapidly induce protective immunity. There is thus a strong incentive to develop more effective vaccines which will provide better protection against early stages of virus infection. This invention relates to a novel genetically engineered vaccine against FMD which provides superior protection over existing commercial vaccines.

2. Description of the Related Art

Genetically-engineered vaccines produced according to conventional recombinant procedures are well-established in the art (as described, for example, in *Current Protocols in Molecular Biology*. 1994. Ausubel et al., eds. J. Wiley & Sons, NY). In addition, vectors containing particular DNAs of interest are increasingly being utilized for the delivery of genetic material for expression in vivo (Ricigliano et al., U.S. Pat. No. 5,795,872). For example, adenovirus is a double-stranded, linear DNA virus approximately 36 kilobases in length, and vectors constructed from adenoviruses are being used to express genes of interest for use in gene therapy and vaccine development (Alkhatib and Briedis. 1988. *J. Virol.* vol. 62, pp. 2718-2727; Chang et al. 1995. *Mol. Med.* vol. 1, pp. 172-181; Cheng et al. 1992. *J. Virol.* vol. 66, pp. 6721-6727; Chengalvala et al. 1994. *J. Gen. Virol.* vol. 75, pp. 125-131; Eloit and Adam. 1995. *J. Gen. Virol.* vol. 76, pp. 1583-1589; Fueyo et al. 1996. *Oncogene.* vol. 12, pp. 103-110; Gahery-Segard et al. 1997. *Eur. J. Immunol.* vol. 27, pp. 653-659; Gonin et al. 1995. *Vet. Microbiol.* vol 45, pp. 393-401; Graham and Prevec. 1992. In *Vaccines: New Approaches to Immunological Problems*. Ellis, R. W., ed., Butterworth-Heinemann, Massachusetts, pp. 363-390; Jacobs et al. 1992. *J. Virol.* vol. 66, pp. 2086-2095; Karlsson et al. 1985. *Proc. Natl. Acad. Sci. USA*. vol. 82, pp. 158-162; Konishi et al. 1995. *J. Clin. Invest*. vol. 96. pp. 1125-1130; Korst et al. 1995. *Am. J. Respir. Crit. Care Med*. vol. 151, pp. S75-S87; Luback et al. 1989. *Proc. Natl. Acad. Sci. USA*. vol. 86, pp. 6763-6767; Mayr et al. 1999. *Virology*. vol. 263, pp. 496-506; Mayr et al. 2001. *Vaccine*. vol. 19, pp. 21552-2162; Muhlhauser et al. 1995. *Circ. Res*. vol. 77, pp. 1077-1086; Papp et al. 1997. *J. Gen. Virol.* vol. 78, pp. 2933-2943; Prevec et al. 1990. *J. Infec. Dis*. vol. 161, pp. 27-30; Prevec et al. 1989. *J. Gen. Virol.* vol. 70, pp. 429-434; Rosenfeld et al. 1991. *Science*. vol. 252, pp. 431-434; Sheppard et al. 1998. *Arch. Virol*. vol. 143, pp. 915-930; Smith et al. 1991. *Mol. Endocrinol*. vol. 5, pp. 867-878; Zabner et al. 1993. *Cell*. vol. 75, pp. 207-216; He et al., U.S. Pat. No. 5,922,576). Most of these systems make use of one adenovirus in particular, human adenovirus serotype 5 (Ad5).

Human Ad5-replication-defective constructs contain deletions in the E1 region resulting in virus which can only replicate in cells that have been stably transfected with the E1 region of the adenovirus genome, i.e., 293 cells (Graham et al. 1977. *J. Gen. Virol.* vol. 36, pp. 59-74). Likewise, many of these vectors contain a deletion in the E3 region, that results in a loss of inhibition of the MHC class I response, leading to an increase in the ability of animals infected by these viruses to develop an immune response to the expressed foreign genes (Chengalvala et al., supra). The loss of approximately 3000 bp of coding sequence in the E1 region, and approximately 2700 bp in the E3 region, when added to the estimated 105% of genome size which adenovirus can package (approximately an additional 1800 bp), gives vectors the ability to contain about 7500 bp of foreign sequence. This construct thus provides a useful model for the design of a vaccine requiring gene expression in vivo.

Type I interferons, IFN $\alpha$ and $\beta$ or IFN $\alpha/\beta$, are known to have antiviral activity and are the first line of host cell defense against virus infection (Vilcek and Sen. 1996. In *Virology*, Fields et al., eds. Lippincott-Raven Publishers, Philadelphia). Virus-infected cells are induced to express and secrete IFN $\alpha/\beta$ which binds to specific receptors on neighboring cells, priming them to a virus resistant state via a series of events leading to activation of IFN $\alpha/\beta$ stimulated genes (ISGs). The products of these genes affect viruses at different stages of their replication cycle, and different viruses are susceptible to different ISG products. Examples of ISGs that have been extensively characterized include double-stranded (ds) RNA dependent protein kinase (PKR), 2'-5'A synthetase/RNase L and Mx.

It has been demonstrated that FMDV replication is highly sensitive to IFN-$\alpha$ or -$\beta$ and that supernatant fluids containing porcine or bovine IFN $\alpha/\beta$ inhibit FMDV replication (Chinsangaram et al. 1999. *J. Virol.* vol. 73, pp. 9891-9898). To study the effect of IFN-$\alpha$ and -$\beta$ on FMDV replication more directly, IFN $\alpha/\beta$ genes from porcine kidney (PK) and embryonic bovine kidney (EBK) cells were amplified and cloned using primers with consensus sequences specific to IFN-$\alpha$ and -$\beta$ for each species. A clone of each IFN was sequenced and expressed in *Escherichia coli* (Chinsangaram et al. 2001. *J. Virol.* vol. 75, pp. 5498-5503, see FIG. 1). At maximal induction, bovine IFN-$\alpha$ and -$\beta$ and porcine IFN-$\alpha$ were expressed at similar levels while porcine IFN-$\beta$ was expressed at a lower level (Chinsangaram et al., supra, 2001, see FIG. 1). When treated at pH 2.0, serially diluted, and tested for biological activity, porcine and bovine IFN-$\alpha$ or -$\beta$ provided a similar inhibitory effect on FMDV replication in cells from homologous species, including a pig kidney cell line (IBRS2) and EBK cells (Chinsangaram et al., 2001, supra, see Table 1). As expected, the control *E. coli*-expressed FMDV protein 3C, had no inhibitory effect on virus replication (Chinsangaram et al., 2001, supra). Expressed porcine and bovine IFN-$\alpha$ or -$\beta$ also had similar antiviral activity against vesicular stomatitis virus (VSV), encephalomyocarditis virus and classical swine fever virus. In addition, it was found that, with the exception of bovine IFN-$\beta$, porcine and bovine IFN-α and porcine IFN-β could also inhibit FMDV replication in cells from the other species (Chinsangaram et al., 2001, supra, see Table 1).

Since FMDV replication in cell culture is sensitive to IFN-α and -β treatment, type I IFN may be useful as an in vivo anti-FMDV agent. It acts rapidly, and its administration should provide protection against all serotypes and subtypes of FMDV, a concern because of the antigenic diversity of FMDV. However, IFNα/β protein is rapidly cleared, and clinical use thus requires multiple injections of high doses for a prolonged period of time. Constructs comprising type I IFN genes provide an alternative means to deliver IFN protein, thus allowing animals to produce IFN endogenously for a period of time. In addition, the amount of IFN delivered can be controlled by the recombinant virus dosage. Vectors, such as recombinant replication-defective human adenoviruses, containing these genes are also effective for delivery and subsequent gene expression in vivo.

SUMMARY OF THE INVENTION

We have constructed a recombinant replication-defective vector containing an interferon gene which is particularly useful for conferring early protection on susceptible animals. One day after inoculation with this vector, animals have been found protected from challenge with virulent foot-and-mouth disease virus (FMDV). By including IFN in a vaccine, early protection prior to development of specific immunity occurs, a feature especially desirable during an FMD outbreak.

Accordingly, it is an object of the invention to provide a novel construct useful as an effective vaccine for early protection of susceptible animals against FMDV by expression of IFN-α or -β.

It is an additional object of the invention to provide a vector containing the novel construct for expression of IFN-α or IFN-β in vivo useful as an effective vaccine for early protection of susceptible animals against FMDV by expression of IFN-α or -β.

It is another object of the invention to provide an effective vaccine for FMDV comprising the novel construct containing the gene encoding IFN-α or IFN-β in a physiologically acceptable carrier and an effective vaccine for FMDV.

It is also an object of the invention to provide a method for the immunization of susceptible animals by administering an effective dosage of a composition comprising the novel construct and a physiologically acceptable carrier.

It is a further object of the invention to provide a method for the immunization of animals susceptible to FMD by administering a composition comprising an effective dosage of the vector containing the novel construct and a physiologically acceptable carrier and an effective vaccine for FMDV.

Other objects and advantages of the invention will become readily apparent from the following description.

BRIEF DESCRIPTION OF THE DRAWINGS

FIG. 1 shows DNA sequences for porcine interferon-α (pIFN-α). Panel A shows the sequence for pIFN-α clone 7 containing the signal sequence (SEQ ID NO: 1). This clone was sequenced in pTOPO, digested with PstI and BamHI and ligated into similarly digested KSII. Subsequently the plasmid was digested with ClaI and XbaI and ligated into ClaI/XbaI digested pAd5-Blue. The virus derived from this plasmid is termed Ad5-pIFNα7.6.3. Panel B shows the sequence for pIFN-α clone 9 containing the signal sequence (SEQ ID NO: 2). This clone was sequenced in pTOPO, digested with PstI and SpeI and ligated into similarly digested KSII. Subsequently the plasmid was digested with ClaI and XbaI and ligated into ClaI/XbaI digested pAd5-Blue. The virus derived from this plasmid is termed Ad5-pIFNα9.9.6.

FIG. 2 shows the DNA sequence for porcine interferon-β (pIFN-β) clone 1 containing the signal sequence (SEQ ID NO: 3). The clone was sequenced in pTOPO, digested with EcoRV and BamHI and ligated into similarly digested KSII. Subsequently the plasmid was digested with ClaI and XbaI and ligated into ClaI/XbaI digested pAd5-Blue. The virus derived from this plasmid is termed Ad5-pIFNβ1.4.6.

FIG. 3 shows the DNA sequence for bovine interferon-α (bIFN-α) clone 9 containing the signal sequence (SEQ ID NO: 4). This clone was sequenced in pTOPO, digested with BamHI and EcoRV and ligated into similarly digested KSII. Subsequently the plasmid was digested with ClaI and XbaI and ligated into ClaI/XbaI digested pAd5-Blue. The virus derived from this plasmid is termed Ad5-bIFNα9.2.2.

FIG. 4 shows the DNA sequence for bovine interferon-β (bIFN-β) clone 5 containing the signal sequence (SEQ ID NO 5). This clone was sequenced in pTOPO, digested with BamHI and EcoRV and ligated into similarly digested KSII. Subsequently the plasmid was digested with ClaI and XbaI and ligated into ClaI/XbaI digested pAd5-Blue. The virus derived from this plasmid is termed Ad5-bIFNβ5.3.1.

FIG. 5 shows the kinetics of expression of pIFN-α in Ad5pIFN-α infected IBRS cells by radioimmunoprecipitation (RIP). Samples were taken at hours post infection (hpi) 4.5, 6, 25 and 30.

FIG. 11 shows serological and clinical response after challenge in animals inoculated with low dose Ad5-pIFN-α. Response is indicated by antiviral activity, viremia, lesions scored and FMDV neutralizing antibodies produced.

FIG. 12 shows serological and clinical response after challenge in animals inoculated with high dose Ad5-pIFN-α. Response is indicated by antiviral activity, viremia, lesions scored and FMDV neutralizing antibodies produced.

FIG. 14 shows the effect of Ad5-IFN-α inoculation on protection of swine from FMDV challenge in the control group. Effects are determined by antiviral activity, viremia, lesions scored and FMDV neutralizing antibodies produced.

FIG. 16 shows the effect of Ad5-pIFN-α inoculation on protection of swine from FMDV challenge in Group 2 (administration 5 days prechallenge). Effects are determined by antiviral activity, viremia, lesions scored and FMDV neutralizing antibodies produced.

FIG. 17 shows the effect of Ad5-pIFN-α inoculation on protection of swine from FMDV challenge in Group 2 (administration 3 days prechallenge). Effects are determined by antiviral activity, viremia, lesions scored and FMDV neutralizing antibodies produced.

FIG. 18 shows the effect of Ad5-pIFN-α inoculation on protection of swine from FMDV challenge in Group 2 (administration 1 day prechallenge). Effects are determined by antiviral activity, viremia, lesion scored and FMDV neutralizing antibodies produced.

FIG. 20 shows the RIP of 14 dpc sera from swine inoculated with Ad5-pIFN-α and challenged various days later.

FIG. 21 shows the protection of swine from direct inoculation challenge with FMDV in a control group administered Ad5-VSVG. Protective effects are determined by antiviral activity, viremia, lesions scored and FMDV neutralizing antibodies produced.

FIG. 22 shows the protection of swine from direct inoculation challenge with FMDV (effect of Ad5-A24). Protective effects are determined by antiviral activity, viremia, lesions scored and FMDV neutralizing antibodies produced.

FIG. 23 shows the protection of swine from direct inoculation challenge with FMDV (effect of Ad5-pIFN-α). Protective effects are determined by antiviral activity, viremia, lesions scored and FMDV neutralizing antibodies produced.

FIG. 24 shows the protection of swine from direct inoculation challenge with FMDV (effect of Ad5-pIFN-α and Ad5-A24). Protective effects are determined by antiviral activity, viremia, lesions scored and FMDV neutralizing antibodies produced.

FIG. 26 shows the effect of Ad5-pIFN-α administration of protection of cattle from challenge with FMDV.

DETAILED DESCRIPTION OF THE INVENTION

Figure 6:
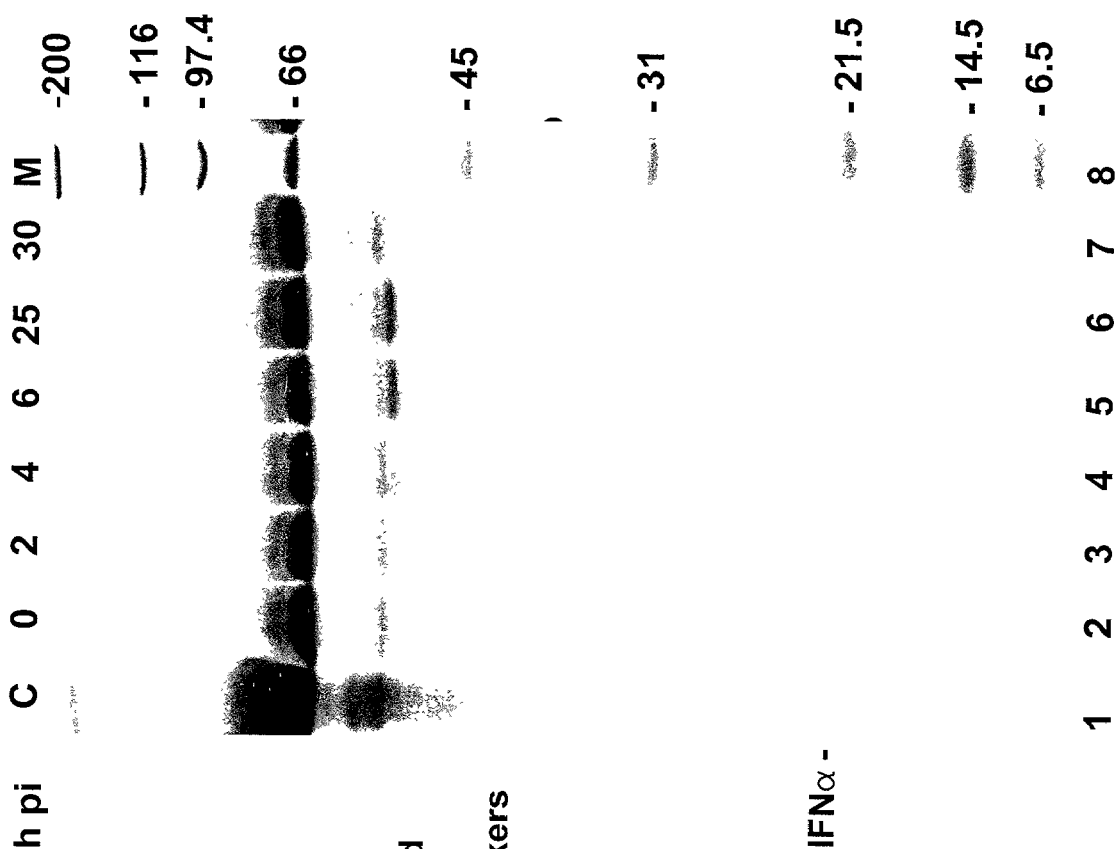
FIG. 6 shows the kinetics of expression of pIFN-α in Ad5-pIFN-α infected IBRS2 cells. Samples were taken at 0, 2, 4, 6, 25 and 30 hpi.

A vaccine is defined herein as a biological agent which is capable of stimulating a protective response in an animal to which the vaccine has been delivered and encompasses any protective response including but not limited to immune responses, both cellular and humoral. In this application, the protective response conferred by IFN is considered effective if it delays either the onset of disease or the severity of the disease sufficient to allow conventional FMD vaccines to stimulate a subsequent protective response in an exposed animal.

A recombinant vaccine comprises a construct effective as a vaccine in vaccination protocols and comprises at least one regulatory element, such as a promoter (e.g. CMV promoter), the SV40 polyadenylation signal sequence, a termination sequence, operably linked to a heterologous DNA sequence which encodes the agent which stimulates the protective response. The construct is prepared according to recombinant methods well known in the art and is capable of expressing a sufficient amount of the immunizing agent to elicit the protective response.

The construct may be inserted into a vector which is useful for immunization or vaccination protocols. The required sequences may be inserted into the vector individually or may be ligated together for insertion as a cassette.

The vaccine of the invention is a composition comprising the construct or the vector containing the construct and a physiologically acceptable carrier, such as phosphate buffered saline, physiological saline or culture medium. The construct may contain sequences which encode IFN-α, IFN-β, or a combination thereof. Sequences which encode an appropriate FMDV antigen may also be included in the construct for convenient co-administration of both the IFN and FMDV antigens or as a separate construct. Such antigens are generally known to those of skill in the art. Examples of effective recombinant vaccines are the leader-proteinase deleted foot-and-mouth disease viruses as described in Grubman et al. (U.S. Pat. No. 5,824,316) and non-infectious FMDV prepared as described in Mason et al. (U.S. Pat. No. 5,612,040). The non-infectious virus is a mutant virus from which the amino acid sequence GVRGDF from the G-H loop of VP1 has been deleted and replaced with the amino acid sequence NP. Alternatively, the vaccine may contain a mixture of IFN-containing vector and an effective FMD vaccine or separate construct for convenient administration.

The vaccine may be administered by intramuscular, intradermal subcutaneous or intranasal inoculation or injection in an amount which is effective for the expression of a sufficient amount of IFN to provide antiviral activity and protect the animal against challenge by a virulent strain of FMDV. This amount may vary according to the animal being inoculated, taking into consideration the size and weight of the animal and the type of IFN. An effective amount for the vaccination of swine, for example, ranges from about $10^8$ to about $10^{10}$, preferably about $10^8$ to about $10^9$, pfu Ad5-IFN. For cattle, an effective amount ranges from about $10^9$ to about $10^{10}$ pfu ad5-IFN. Effective amounts may be experimentally determined as necessary by those of skill in the art by following the guidance provided by specific Examples 1-14.

A recombinant vaccine containing IFN is prepared by inserting an IFN-α or -β cDNA construct into an effective vector. Sequences encoding FMDV antigens may also be included in the inserted construct. Effective systems for the delivery of genetic material into tissues in vivo are well-known to those of skill in the art and include viral as well as nonviral transfer methods (e.g. Ricigliano, supra). The use of viral gene transfer vectors has been widely disclosed in the art and includes the use of adenovirus, adeno-associated virus, parvovirus, vaccinia virus, herpesvirus, poxvirus, poliovirus and a number of retroviruses. While any of the known vectors may be successfully utilized for delivery of IFN, the adenovirus vector described herein (Ad5) has been utilized for purposes of experimentation and therefore presented by way of example.

It is also contemplated that the vaccine may comprise the construct containing sequences encoding IFN, and FMDV antigens if desired, in a physiologically acceptable carrier. Alternatively, the vaccine may be a mixture of the contruct containing sequences encoding IFN and a known effective FMDV vaccine.

The IFN-containing vaccine is prepared according to known recombinant techniques. First, the appropriate IFN gene is cloned, then inserted into the selected vector. Specific examples are provided herein in order to provide guidance to those of skill in the art. Appropriate IFN genes are Type I IFN α/β obtained from any animal susceptible to FMD, which includes any cloven-hooved animal such as swine, cattle and sheep. The vaccine provides rapid, short-term protection against FMD and other viral agents. By co-administering IFN-containing vaccine with known and conventional FMD vaccines, both short- and long-term protection is provided.

Porcine IFN-α or -β cDNAs were inserted into the E1 region of replication-defective human adenovirus type 5 (Ad5) genome by direct ligation, and the chimeric DNA was used to transfect 293 cells, expressing E1 function, to produce recombinant adenoviruses (Ad5-pIFNα or Ad5-pIFNβ, as described in Examples 1-5.

As detected by polyacrylamide gel electrophoresis (PAGE) and Coomassie blue staining, both IFN molecules were expressed to high levels in an Ad5-pIFNα or Ad5-pIFNβ-infected pig kidney cell line (IBRS2) that does not support productive replication of replication-defective adenovirus. The specificity was confirmed using rabbit anti-porcine IFN-α or -β antibodies in radioimmunoprecipitation assays. Supernatants from Ad5-pIFNα-infected IBRS2 cells provide more that $10^5$ units of antiviral activity to homologous cells as determined by a FMDV plaque reduction assay. Intramuscular inoculation of pigs with $10^8$ or $10^9$ pfu of Ad5-pIFNα resulted in greater than approximately 400 units of antiviral activity in plasma samples at the earliest time examined, i.e. at 16 hours postinoculation.

Experimental results have demonstrated that swine are rapidly protected from FMD by inoculation with Ad5-pIFN-α (see Example 8). Furthermore, data demonstrating antiviral activity for at least 5 days after inoculation with the high dose of Ad5-pIFN-α suggest that animals may be protected for at least this time period.

The following examples are intended only to further illustrate the invention and are not intended to limit the scope of the invention as defined by the claims.

All references cited herein are herein incorporated by reference in their entirety.

EXAMPLES

Example 1

Bacterial Strains and Mammalian Cell Lines.

Adenovirus plasmids and pAd-Blue (Moraes et al. 2001. *BioTechniques*. vol. 31, pp. 1050-1056) were propagated in electrocompetent cells (Invitrogen One Shot TOP10 Electrocomp™ Cells, Invitrogen, Carlsbad, Calif., USA). Other vectors were grown in chemically competent TOP10 cells (Invitrogen One Shot TOP10, supra). Prior to design of the pAd5-Blue vector, a precursor vector containing foreign genes had been constructed using homologous recombination in competent BJ5183 cells following the manufacturer's protocols (Quantum Biotechnologies, Montreal, Canada).

Recombinant adenoviruses derived from pAd5-Blue vectors were grown in and purified from 293 cells (Graham et al., supra). A plasmid containing the VSV-NJ glycoprotein (G) gene (pCR-Blunt II-TOPO-VSV G) was provided by Dr. Luis Rodriguez).

Example 2

Cloning of Type I Interferon Genes.

Swine and bovine IFN-α and -β genes were amplified from DNA (since IFN genes contain no introns) or cDNA obtained from porcine kidney (PK) and embryonic bovine kidney (EBK) cells, respectively, utilizing primers based on available Genbank sequences. The 5' primer contained the IFN secretory signal sequence, and the 3' primer contained a stop codon followed by a BamHI restriction endonuclease site. The genes were amplified for 25 cycles utilizing the polymerase chain reaction (PCR) with Pfu polymerase and the appropriate primers (Table 1). PCR products (blunt-ended) were ligated into linearized pCR-BluntII-TOPO and transformed into TOP10 cells. Clones were examined by restriction endonuclease digestion, and clones containing the appropriately sized inserts were sequenced (FIGS. 1-4). Clones for more than one IFN-α and -β gene were obtained, since all animal species examined have large IFN-α subfamilies, and pigs and cows have at least five interrelated IFN-β genes (Vilcek and Sen, supra). The IFN sequences in FIGS. 1-4 represent the genes used to produce recombinant adenoviruses (see Example 4). Recombinant adenovirus Ad5-pIFNα7.6.3 is derived from the sequence of FIG. 1*a* (SEQ ID NO: 1), Ad5-pIFNα9.9.6 from the sequence of FIG. 1*b* (SEQ ID NO: 2), Ad5-pIFNβ1.4.6 from the sequence of FIG. 2 (SEQ ID NO: 3), Ad5-bIFNα9.2.2 from the sequence of FIG. 3 (SEQ ID NO: 4) and Ad5-bIFNβ 5.3.1 from the sequence of FIG. 4 (SEQ ID NO: 5).

Example 3

Expression of IFN-Containing Plasmids.

Plasmids containing porcine IFN-α clones 7 and 9 (FIG. 1) and IFN-β clone 1 (FIG. 2) were digested with different restriction endonucleases and ligated into similarly digested pBluescript II KS+ (pKSII) (Stratagene, LaJolla, Calif.). Clones in the correct orientation were examined for expression by

TABLE 1

Primers for the Amplification of Bovine and Porcine IFN

| | | |
|---|---|---|
| BOVINE IFN-α FORWARD: | 5'CCG ATG GCC CCA GCC TGG TCC | (SEQ ID NO: 6) |
| BOVINE IFN-α REVERSE: | 5'GGA TGG ATC CTC AGT CCT TTC TCC TGA AWY TCT C | (SEQ ID NO: 7) |
| BOVINE IFN-β FORWARD: | 5'CAT CAT GAC CYA CCG GTG CCT CCT CC | (SEQ ID NO: 8) |
| BOVINE IFN-β REVERSE: | 5'GGA TGG ATC CTC AKT CAC GGA SGK AAC CTG TTA G | (SEQ ID NO: 9) |
| PORCINE IFN-α FORWARD: | 5'ATG GCC CCA ACC TCA GCC | (SEQ ID NO: 10) |
| PORCINE IFN-α REVERSE: | 5'TGG ATC CTC ACT CCT TCT TCC TCA GTC TGT C | (SEQ ID NO: 11) |
| PORCINE IFN-β FORWARD: | 5'ATG GCT AAC AAG TGC ATC CTC | (SEQ ID NO: 12) |
| PORCINE IFN-β REVERSE: | 5'GGA TGG ATC CTC AGT TCC GGA GGT AAT CTG TAA G | (SEQ ID NO: 13) |

K = T and G
S = G and C
W = A and T
Y = C and T radiolabeling in an in vitro transcription/translation system (TNT kit, Promega, Madison, Wis.). The in vitro expressed IFN's were immunoprecipitated with polyclonal serum and analysed by polyacrylamide gel electrophoresis (PAGE). One band was observed for both porcine IFN-α and -β (data not shown). Rabbit polyclonal antiserum against porcine and bovine IFNs had previously been produced by expression in an *E. coli* system (Chinsangaram et al., 2001, supra).

Plasmids containing bovine IFN-α clones 8 and 9 (FIG. 3) and bovine IFN-β clones 5 (FIG. 4) and 10 were digested with EcoRV and BamHI and ligated into similarly digested pKSII. Clones were examined for expression in an in vitro TNT system as described for porcine IFN genes. All clones examined expressed one band of the appropriate size (data not shown).

Example 4

Construction of Ad5-IFN Vectors.

A mammalian expression system using a replication-defective human adenovirus 5 vector, pAd5-Blue (Moraes, supra) was developed. This virus contains the alpha fragment of β-galactosidase. The pAd5-Blue vector system allows the generation of recombinant adenoviruses within 3 weeks of obtaining an appropriate foreign gene insert.

The IFN genes from porcine IFN-α clones 7 and 9 (see FIG. 1), porcine IFN-β clone 1 (FIG. 2), bovine IFN-α clone 9 (FIG. 3) and bovine IFN-β (FIG. 4) clone 5 were removed from pKSII by digestion with ClaI/XbaI, and ligated into ClaI/XbaI digested and alkaline phosphatase treated pAd5-Blue. The ligation reaction was electroporated into TOP10 cells and white colonies selected on agar plates containing the appropriate antibiotics in the presence of 5-bromo-4-chloro-3-indolyl-β-D-galactoside (XgaI). DNA was digested with HindIII and analyzed by agarose gel electrophoresis to demonstrate the presence of the IFN genes in the recombinant construct. Large-scale preparations of 1-2 colonies of each pAd5-IFN vector, that have the correct gene fragments after HindIII digestion, were grown and plasmid DNA purified by CsCl centrifugation.

Purified DNA was linearized with PacI and transfected into 293 cells by $CaPO_4$ precipitation (Moraes, supra). Cells were examined daily and plaques picked and amplified by infection of a 150-mm flask of 293 cells. Upon the development of cytopathic effects (CPE), 2-3 days postinfection, virus was isolated as described by Moraes (supra). Viral DNA was extracted and examined by HindIII digestion to confirm the presence of the appropriate gene fragments. These virus preparations (Ad5-pIFN-α, Ad5-pIFN-β, Ad5-bIFN-α and Ad5-bIFN-β) represent high titer crude stocks and were used to prepare large amounts of virus that was purified by discontinuous followed by continuous CsCl gradient centrifugation. Virus titers were determined by a tissue culture infectious dose assay ($TCID_{50}$) in 293 cells and were approximately $10^{10}$ pfu/ml (after conversion to pfu titer).

The same protocol is followed to prepare ovine Ad5-IFN vectors (Ad5-oIFNα and Ad5-oIFNβ).

Example 5

Expression of IFN in Mammalian Cells.

Ad5-pIFNs were examined for IFN expression in IBRS2 cells, a cell line susceptible to infection with replication-defective Ad5 but not productive replication. IBRS2 cells do not produce type I IFN mRNAs after virus infection (Chin-sangaram et al. 2001, supra), and therefore IFN that is detected will be a result of Ad5 infection. Cells were radiolabeled with [$^{35}$S]methionine for 1 hr at various times after infection and supernatants (s) and cell lysates (p) immunoprecipitated (RIP) with the appropriate polyclonal rabbit antibodies and examined by PAGE. As shown for Ad5-pIFNα9.9.6 infected cells, pIFN-α is observed in the supernatant (s) at the earliest time examined, 4.5 hrs postinfection (hpi), as well as at 6, 25, and 30 hpi (FIG. 5). The expressed IFN-α is larger than in vitro translated IFN (lanes c1 and c2), since it is presumably glycosylated. It was expected that IFN would be detected in the cell supernatants, since the expressed IFN contains a signal sequence and will be secreted. Similar results were obtained with Ad5-pIFNα7.6.3 and Ad5-pIFNβ1.4.6 infected IBRS2 cells (data not shown). These results demonstrate that IFN expression begins by 4.5 hpi or earlier and continues at least until 30 hpi.

Infected, unlabeled IBRS2 cells were also monitored for IFN expression in supernatant fluids by PAGE analysis and Coomassie blue staining. Appropriate controls, including mock-infected cells and cells infected with another Ad-vector (Ad5-FMDVA24), were included during analysis of expression. A band migrating slightly slower than *E. coli* expressed pIFN-α was barely detectable by 4 hpi in Ad5-pIFNα7.6.3 infected cells, and increased levels were present at 6 hpi (FIG. 6). In mock-infected and Ad5-FMDVA24 infected cells, no comparable bands were observed (lanes 1 and 2). Two bands corresponding to the molecular weight of pIFN-α were observed at 25 and 30 hpi, perhaps indicating different levels of glycosylation (IFN-α clone 7.6.3 has one potential glycosylation site). IBRS2 cells infected with Ad5-pIFNα9.9.6 resulted in similar kinetics of expression of IFN-α, although IFN was initially observed at 2 hpi (data not shown). In Ad5-pIFNβ1.4.6 infected cells, a broad band was initially observed at 4.5 hpi, perhaps reflecting different levels of glycosylation (pIFN-β clone 1.4.6 has 2 potential glycosylation sites). Preliminary analysis indicates that approximately 25 μg pIFN-α was produced per 1 ml of supernatant fluid. Lesser amounts of pIFN-β were produced (data not shown).

Figure 7:
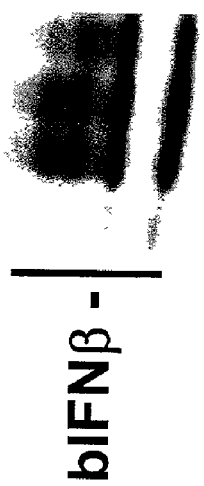
FIG. 7 shows the kinetics of expression of IFN-α and IFN-β in Ad5-bIFN-α or Ad5-bIFN-β infected IBRS2 cells. Samples were taken at 5, 23, 28 and 48 hpi.

For expression of bovine IFN-α and -β genes, IBRS2 cells were infected with Ad5-bIFNα9.2.2 and Ad5-bIFNβ5.3.1 and cells radiolabeled with [$^{35}$S]methionine for 1 h at various times postinfection. Supernatant fluids and cell lysates were either directly examined by PAGE or immunoprecipitated with rabbit polyclonal antisera against bovine IFN-α or bovine IFN-β. Expression was observed by 23 hpi (very low levels at 5 hpi) and continued for at least 48 h (FIG. 7). Immunoprecipitation of bovine IFN-α revealed a single band, while multiple bands of bovine IFN-β were immunoprecipitated presumably indicating various levels of glycosylation (data not shown). Expression was also monitored in infected IBRS2 supernatant fluids by PAGE analysis and Coomassie blue staining. A band corresponding to bIFN-α was initially visible by 5 hpi, and significant levels were detected by 23 hpi. Preliminary analysis indicates that approximately 12-25 μg bIFN-α and approximately 5 μg bIFN-β was produced per 1 ml of supernatant fluid.

Example 6

Antiviral Activity Induced by IFN-α and IFN-β Genes in Infected Cells.

To demonstrate antiviral activity by pIFN-α and pIFN-β genes, supernatant fluids from Ad5-IFNα7.6.3, Ad5-pIFNα9.9.6 and Ad5-pIFNβ1.4.6 infected IBRS2 cells were filtered through a Centricon 100 filter to remove the majority of the Ad5 inoculum remaining (this procedure removes $10^4$-$10^5$ pfu virus) and treated at pH 2 overnight (this procedure inactivates $10^2$-$10^3$ pfu virus) and neutralized to further eliminate the Ad5 inoculum. Supernatants were assayed for antiviral biological activity by a plaque reduction assay on IBRS2 cells with FMDV type A12 (Chinsangaram et al., 1999, supra). Antiviral activity was initially detected between 2-4 hpi in Ad5-pIFNα7.6.3, Ad5-pIFNα9.9.6 and Ad5-pIFNβ1.4.6 infected cell supernatants and by 25 hpi was between 64-256,000 units of activity (Table 2). Supernatant fluids from Ad5-FMDVA24 infected IBRS2 cells (24 hpi) and mock-infected cells were included as controls and had no detectable antiviral activity (data not shown).

Supernatant fluids produced in Ad5-pIFN-α and Ad5-pIFN-β infected IBRS2 cells were assayed in both IBRS2 and MDBK cells (a bovine cell line). As shown in Table 3, supernatant fluids containing either pIFN-α or pIFN-β had equivalent activity in swine and bovine cell lines. The decreased antiviral activity induced by pIFN-β compared to pIFN-α may be related to its lower level of expression.

TABLE 2

Antiviral Activity in Supernatants[a] of Ad5-pIFN-α or Ad5-pIFN-β Infected IBRS2 Cells.

| Time post infection (h) | Ad5-Vector | | |
|---|---|---|---|
| | Ad5-pTFNα7.6.3 | Ad5-pIFNα9.9.6 | Ad5-pIFNβ1.4.6 |
| 1 | <50[b] | <50 | <50 |
| 2 | <50 | <50 | <50 |
| 4 | 800 | 400 | 200 |
| 6 | 3200 | 3200 | 1600 |
| 25 | 256,000 | 128,000 | 64,000 |

[a]Supernatants were centrifuged through a Centricon 100 membrane, pH 2 treated and neutralized, and assayed for antiviral activity
[b]Highest dilution that reduced FMDV plaque number by 50% in IBRS2 cells

TABLE 3

Antiviral Activity of Supernatants[a] from Ad5-pIFN-α and Ad5-pIFN-β Infected IBRS2 Cells on Swine and Bovine Cells.

| Time post infection (h) | Ad5-Vector | | | |
|---|---|---|---|---|
| | Ad5-pIFNα7.6.3 Cell Type | | Ad5-pIFNβ1.4.6 Cell Type | |
| | IBRS2[b] | MDBK[c] | IBRS2 | MDBK |
| 1 | <50 | <50 | <50 | <50 |
| 2 | <50 | <50 | <50 | <50 |
| 4 | 800 | 400 | 200 | 100 |
| 6 | 3200 | 3200 | 1600 | 400 |
| 25 | 256,000 | 123,000 | 64,000 | 32,000 |

[a]Supernatants were centrifuged through a Centricon 100 membrane, pH 2 treated and neutralized, and assayed for antiviral activity
[b]Highest dilution that reduced FMDV A12 plaque number by 50%
[c]Highest dilution that reduced VSV-NJ plaque number by 50%

To determine antiviral activity by bIFN-α and bIFN-β genes, supernatant fluids from Ad5-bIFNα9.2.2 and Ad5-bIFNβ5.3.1 infected IBRS2 cells were treated as described to remove any residual Ad5. Treated supernatants were assayed for antiviral activity on both MDBK and IBRS2 cells. Antiviral activity was detectable by 5 hpi and reached levels of approximately 204,000 units/ml 28-48 hpi (Table 4). As demonstrated, bIFN-α has equivalent biological activity in both bovine and swine cells, while bIFN-β was only active in the bovine cell (Chinsangaram, 1999, supra).

TABLE 4

Antiviral Activity of Supernatants[a] from Ad5-bIFN-α and Ad5-bIFN-β Infected IBRS2 Cells on Bovine and Swine Cells.

| Time Post Infection (h) | Ad5-Vector | | | |
|---|---|---|---|---|
| | Ad5-bIFNα9.2.2 Cell Type | | Ad5-bIFNβ5.1.3 Cell Type | |
| | MDBK[b] | IBRS2[c] | MDBK | IBRS2 |
| 1 | <50 | <50 | 50 | <50 |
| 5 | 3200 | 6400 | 12,800 | <50 |
| 23 | 51,200 | >51,200 | 204,800 | <50 |
| 28 | 102,400 | >102,000 | 204,800 | <50 |
| 48 | 204,800 | 204,000 | 51,200 | 100 |

[a]Supernatants were centrifuged through a Centricon 100 membrane, pH2 treated and neutralized, and assayed for antiviral activity
[b]Highest dilution that reduced VSV-NJ plaque number by 50%
[c]Highest dilution that reduced FMDV A12 plaque number by 50%

Example 7

Expression of IFN in Swine: Test for Safety and Potency.

A dose-response experiment was performed in swine inoculated with Ad5-pIFNα7.6.3, to determine if biologically active IFN was detectable in inoculated animals. Pigs (one for each dose) were inoculated intramuscularly (IM) with $10^7$, $10^8$ or $10^9$ pfu Ad5-pIFN-α7.6.3, and an additional animal inoculated IM with $10^8$ pfu Ad5-VSVG (adenovirus containing the glycoprotein gene of vesicular stomatitis virus, Moraes, supra). Animals were examined for adverse effects from IFN administration, and temperatures were taken daily. Plasma samples were obtained at 16, 18, 20 and 22 hpi and once daily thereafter for an additional 6 days. The samples were examined for antiviral activity by a plaque reduction assay (Chinsangaram et al., 1999, supra).

None of the inoculated animals developed adverse clinical signs or an increase in temperature after inoculation. Neither the Ad5-VSVG-inoculated animal nor the animal inoculated with $10^7$ pfu Ad5-pIFN developed antiviral activity. The animals inoculated with $10^8$ or $10^9$ pfu Ad5-pIFN developed antiviral activity at the earliest time assayed, e.g., 16 hpi. The animal inoculated with $10^9$ pfu Ad5-IFN had 400 units/ml antiviral activity in plasma at 16 hpi and activity continued at this level for 2 days. Antiviral activity decreased over time but was still detectable at 4 dpi.

Example 8

Protection of Swine Inoculated with Ad5-pIFN-α from Infection with FMDV.

Groups of pigs housed in separate rooms (3 per group) were inoculated IM with $10^8$ or $10^9$ pfu Ad5-pIFN-α7.6.3 (Groups 2 and 3) and a control group inoculated with $10^9$ pfu Ad5-Blue (Group 1) (Table 5). The animals were challenged one day later by direct inoculation with $3\times10^5$ 50% bovine infectious dose ($BID_{50}$) FMDV A24 in the heel bulb of the left front foot. Animals were monitored for clinical signs of FMD including fever, viremia and induction of FMDV-specific antibodies until 14 days post challenge (dpc) and antiviral activity for 7 days postinoculation (dpi). Three identical groups of animals were

TABLE 5

Experimental Design.

| Group | Animal Number | Inoculum[a] | Challenge[b] |
|---|---|---|---|
| #1 Ad5-Blue | 304-12, 305-2, 305-3 | $10^9$ pfu Ad5-Blue | $3 \times 10^5$ $BID_{50}$ |
| #2 Low Dose | 186-1, 199-2, 501-3 | $10^8$ pfu Ad5-pIFNα7.6.3 | $3 \times 10^5$ $BID_{50}$ |
| #3 High Dose | 3-1, 3-2, 7-7 | $10^9$ pfu Ad5-pIFNα7.6.3 | $3 \times 10^5$ $BID_{50}$ |
| #4 Ad5-Blue | 367-1, 368-1, 402-1 | $10^9$ pfu Ad5-Blue | No Challenge |
| #5 Low Dose | 204-1, 208-6, 365-4 | $10^8$ pfu Ad5-pIFNα7.6.3 | No Challenge |
| #6 High Dose | 202-4, 202-6, 203-3 | $10^9$ pfu Ad5-pIFNα7.6.3 | No Challenge |

[a]Pigs inoculated IM with indicated dose of Ad5-vector
[b]Pigs challenged 1 day after administration of Ads-vector by inoculation in the heel bulb of the left front foot with the indicated dose of FMDV A24 inoculated as above, but were not challenged with FMDV (Groups 4-6). These animals were monitored for fever and antiviral activity assayed. Results are shown in FIGS. 8-13.

Figure 8:
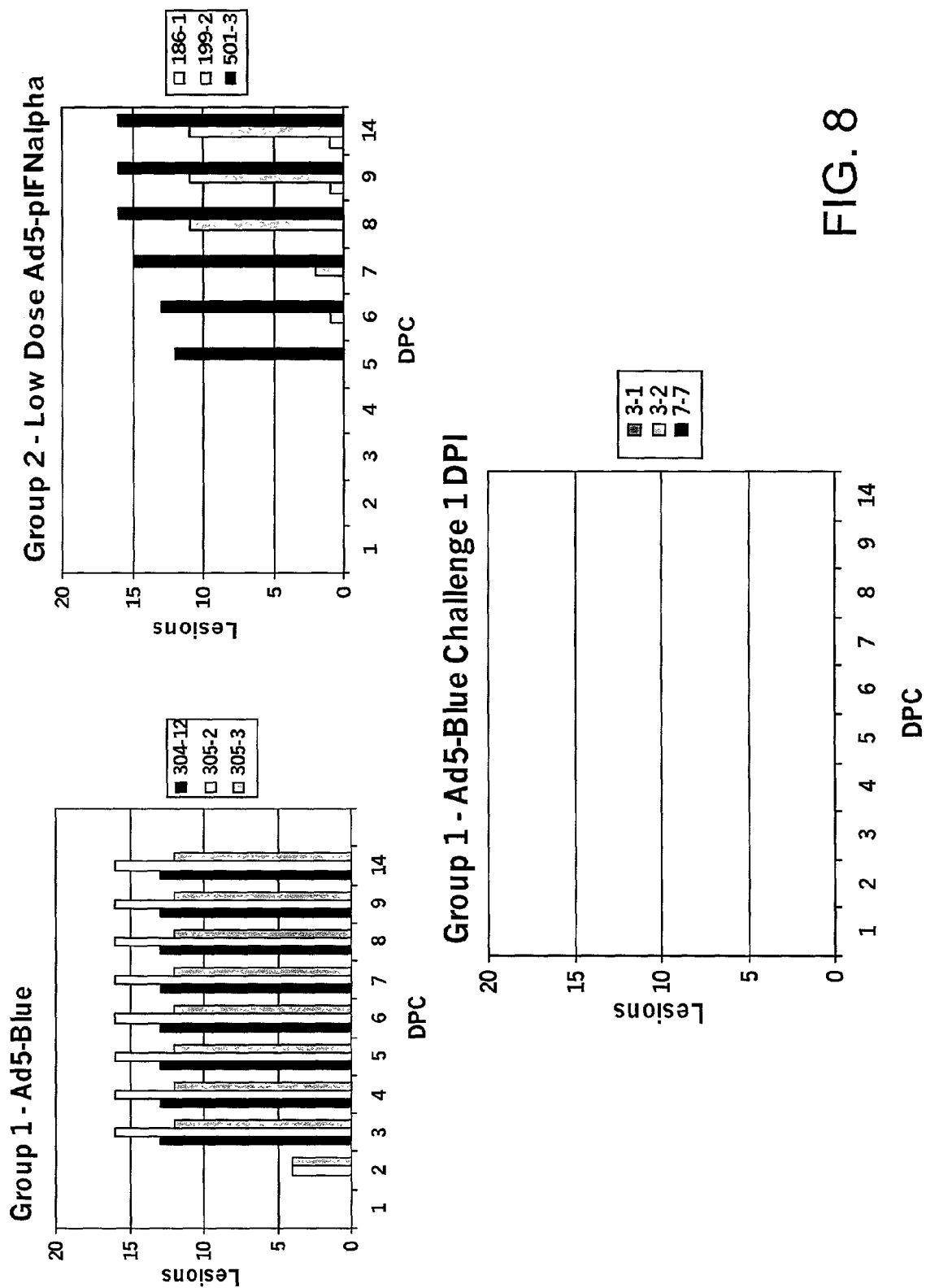
FIG. 8 shows the effect of Ad5-pIFN-α administration on protection of swine from challenge with FMDV. Lesions were scored up to day 14 post challenge. Group I received Ad5-Blue (control); Group 2 received low dose Ad5-pIFN-α.

Clinical response after challenge: Two of the three animals in the control group developed vesicular lesions by 2 dpc, i.e., #305-2 and 305-3, and by 3 dpc all 3 animals had lesions (FIG. 8). All 3 animals had severe disease by 3 dpc. Swine #305-2 developed a fever (temperature of over 104° F.) for 3 consecutive days, while the other 2 animals in this group only developed fever for 1 or 2 days (data not shown). In Group 2, inoculated with $10^8$ pfu Ad5-pIFN-α, #501-3 developed severe FMD by 4 dpc, #199-2 had a lesion by 5 dpc and severe FMD by 7 dpc, and #186-1 only developed 1 lesion on the left rear foot at 8 dpc (FIG. 8). In Group 3, inoculated with $10^9$ pfu Ad5-pIFN-α, none of the animals showed any signs of FMD throughout the course of the experiment, i.e., 14 days after challenge (FIG. 8). Swine #7-7, Group 3, died on day 12 (post challenge). Necropsy revealed no signs of FMD infection and no FMDV was detected in pharyngeal tonsil, heart, lung, left precapsular lymph node, or blood by titration on BHK cells. This animal showed massive peritonitis probably from ileal perforation.

Figure 9:
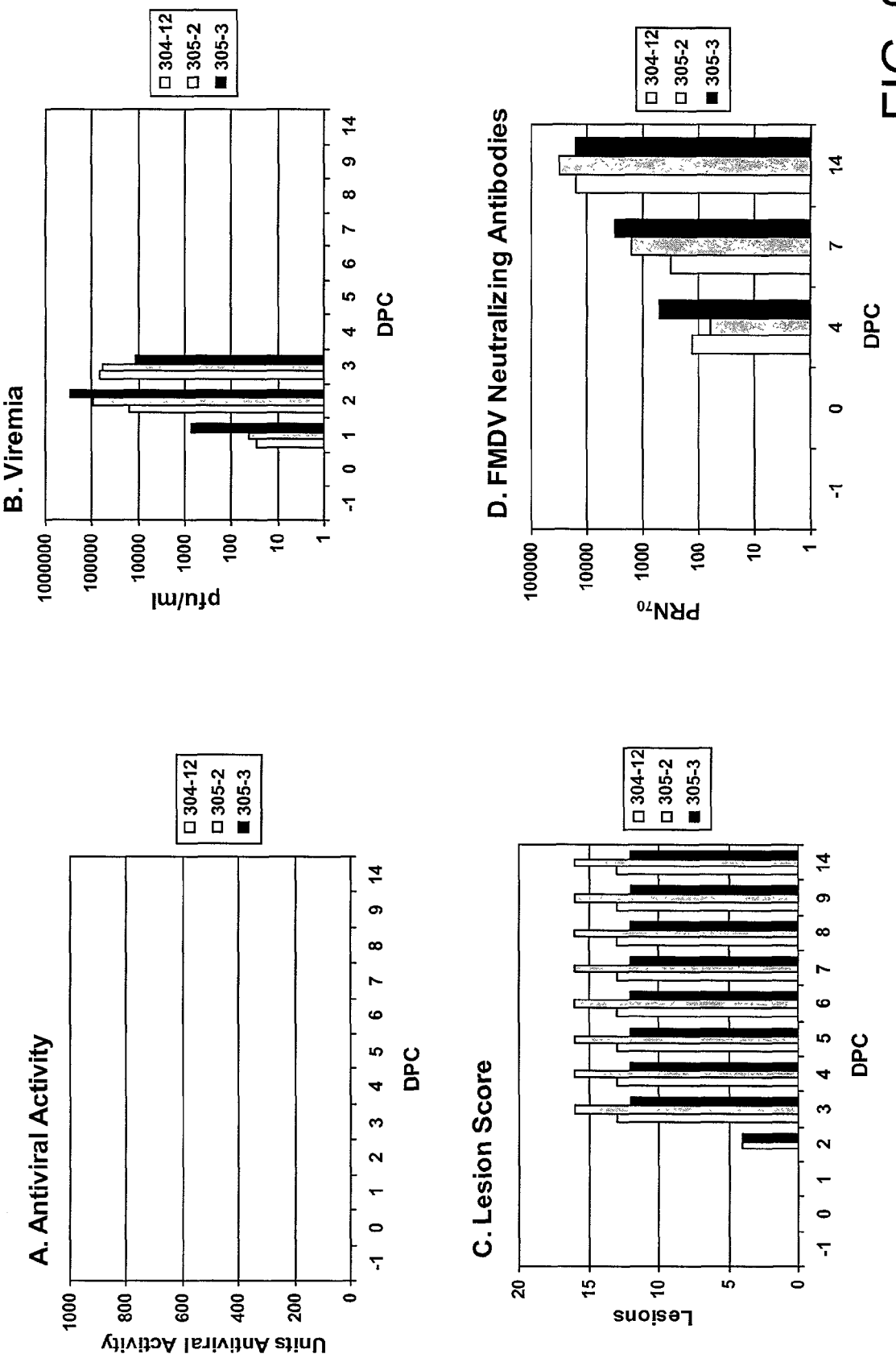
FIG. 9 shows serological and clinical responses after challenge in Ad5-Blue inoculated animals. Response is indicated by antiviral activity, viremia, lesions scored and FMDV neutralizing antibodies produced.
Figure 10:
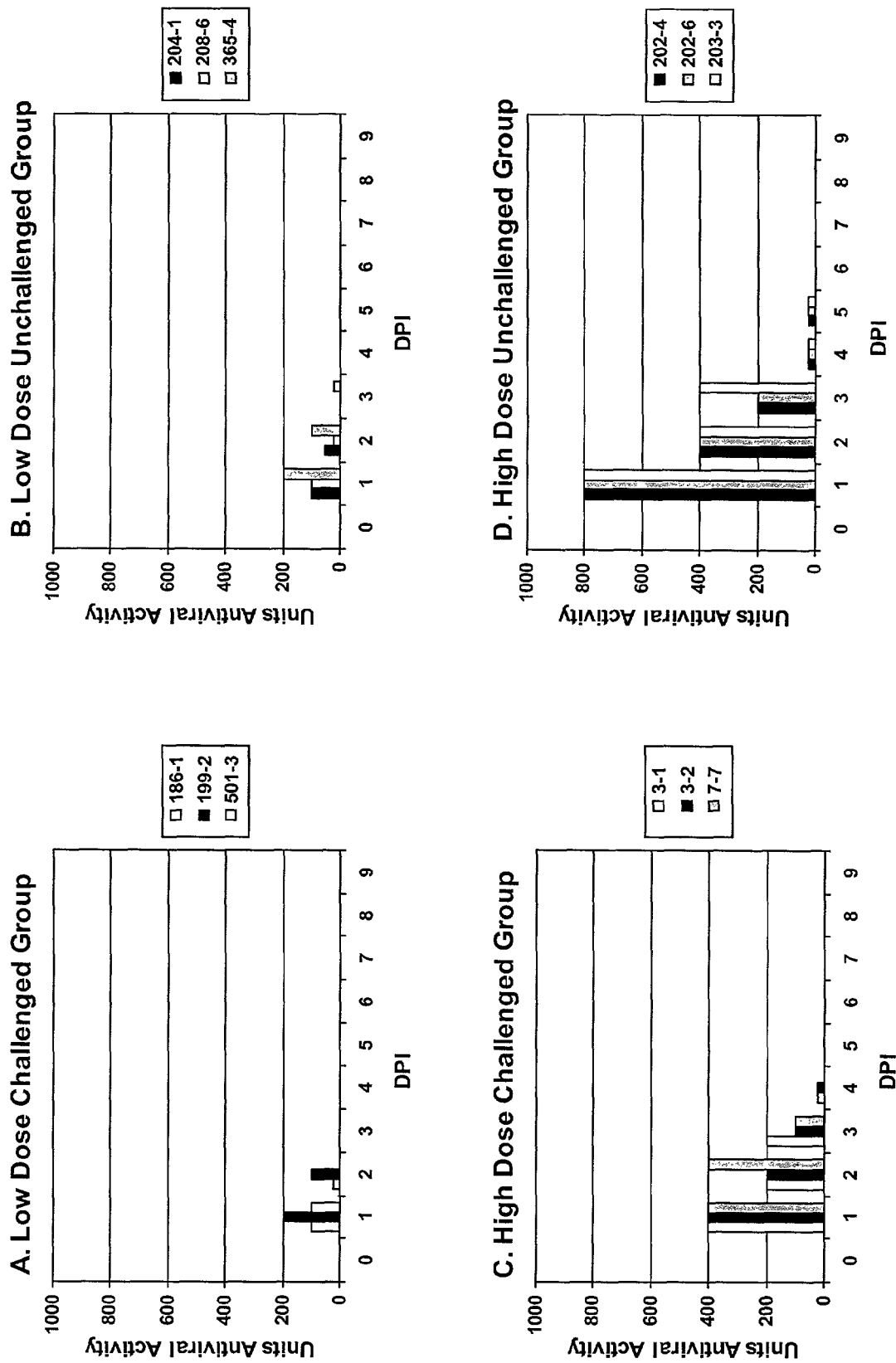
FIG. 10 shows antiviral activity in swine inoculated with low or high dose Ad5-pIFN-α.
Figure 11:
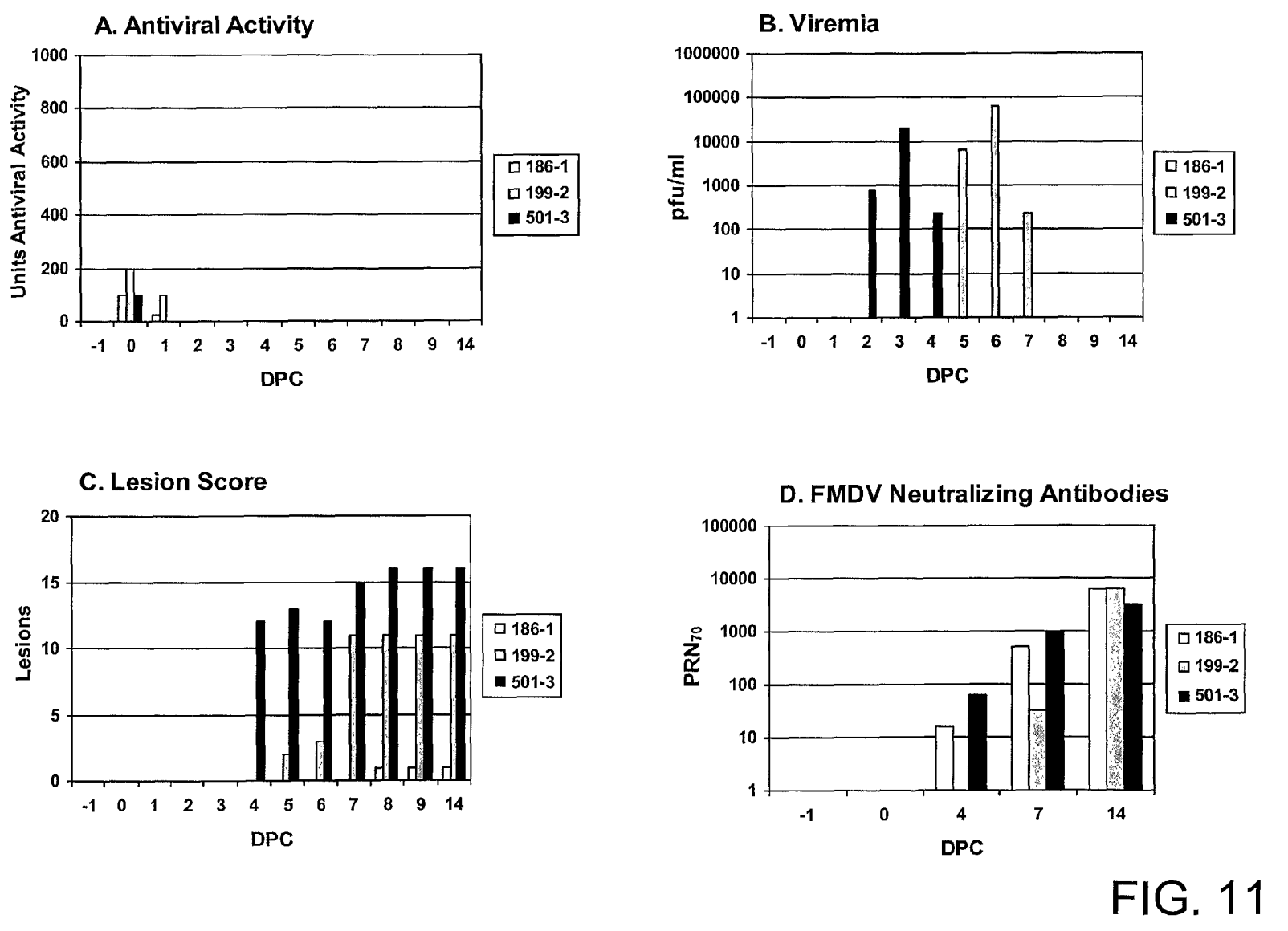

Serological analysis: All the animals in the control group, Group 1, developed viremia by 1 dpc which was detectable until 3 dpc and reached titers of $10^4$-$10^5$ pfu/ml (FIG. 9). These animals developed an FMDV-specific neutralizing antibody response by 4 dpc. Swine #501-3, in Group 2, had detectable antiviral activity, 100 units, only at 1 dpi (−1 dpc), developed viremia at 2 dpc, and lesions by 4 dpc (FIGS. 10A and 11). Swine #199-2 had detectable antiviral activity at 1 dpi (−1 dpc) that lasted for an additional day. This animal had viremia at 5 dpc that continued for 2 additional days, and it developed one lesion at 5 dpc and disease became more extensive at 7 dpc. Swine #186-1 had detectable antiviral activity by 1 dpi (−1 dpc) that lasted for an additional day. This animal did not develop viremia, but had 1 lesion at 8 dpc and had an FMDV-specific neutralizing antibody response by 7 dpc.

Figure 12:
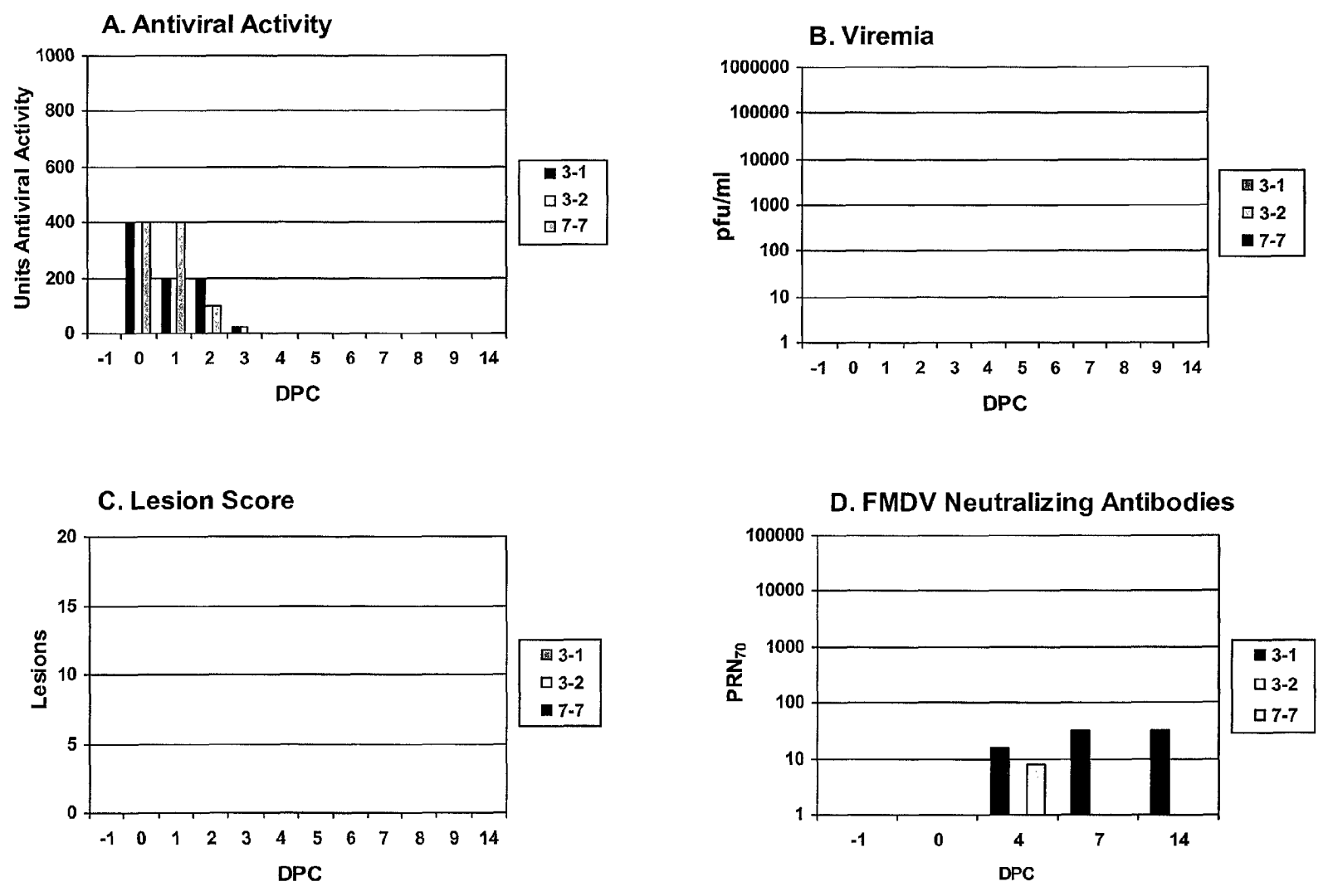

The animals in Group 3 had high levels of antiviral activity at 1 dpi (−1 dpc), 400 units, that was detectable for 2-3 additional days (FIGS. 10C and 12). All the animals in this group were completely protected from virus challenge. None of the animals in the group had viremia.

The animals in Groups 5 and 6 that were not challenged with FMDV generally developed higher levels of antiviral activity that lasted 1-2 days longer than the equivalent FMDV challenged groups (FIGS. 10B and 10D). The Ad5-Blue inoculated animals, control Group 4, did not develop detectable antiviral activity (data not shown). The animals in both groups developed fever for 2-3 days, their temperature returned to normal and they displayed no other adverse clinical signs (data not shown).

Figure 13:
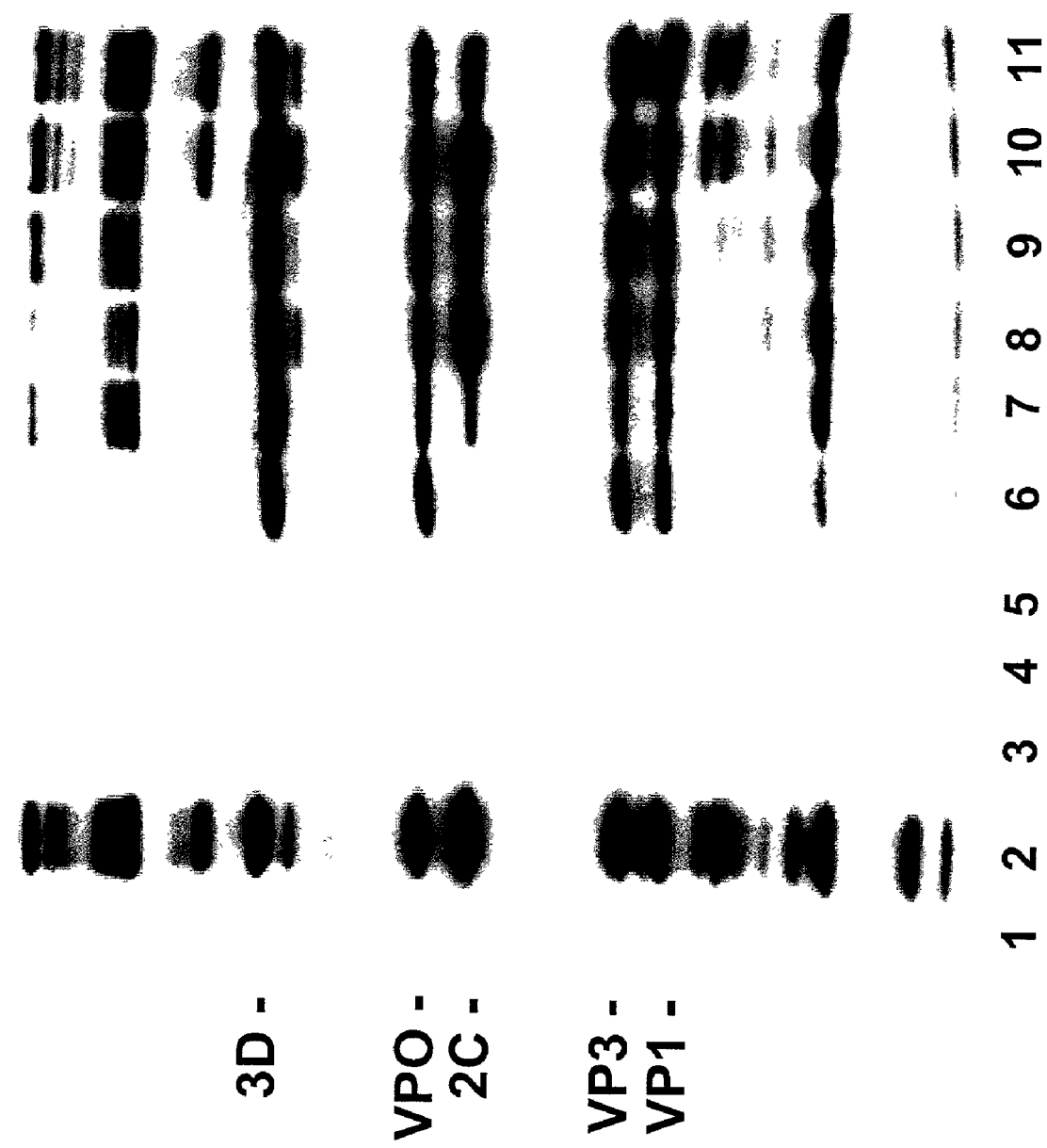
FIG. 13 shows RIP of 14 dpc sera from swine inoculated with Ad5-pIFN-α and challenged 1 day later.

To determine if IFN treatment blocked challenge virus replication, 14 dpc sera from Groups 1-3 were examined by RIP for the presence of antibodies against viral structural and nonstructural (NS) proteins. The ability of sera from challenged animals to immunoprecipitate viral NS proteins is indicative of virus replication in these animals. As expected, the sera from all 3 animals in Group 1 contained antibodies to viral structural and NS proteins (FIG. 13, lanes 9-11). Likewise all animals in Group 2 developed antibodies against viral structural and NS proteins (lanes 6-8). In contrast, all animals in Group 3, which were completely protected from clinical disease and viremia, did not develop antibodies against the viral NS proteins demonstrating that, by this assay, these animals were completely protected from challenge virus replication (lanes 3-5). Assays (3ABC ELISA) on the above sera confirmed the absence of virus replication in Group 3 animals.

Example 9

Duration of Protection of Swine Inoculated with Ad5-pIFN-α from Infection with FMDV.

The experiment described in Example 8 demonstrated that one day after administration of $10^9$ pfu Ad5-pIFN-α, pigs were completely protected from challenge with virulent FMDV A24. To determine how long after Ad5-pIFN-α inoculation animals can be protected from clinical disease and if preinfected animals can be protected from viremia and clinical signs of disease by administration of Ad5-pIFN-α one day later, groups of animals (3 animals/group) were inoculated with $10^9$ pfu Ad5-pIFN-α7.6.3 and challenged with $3.5 \times 10^5$ $BID_{50}$ FMDV A24 in the left rear foot (50 µl/toe) at 1, 3, 5 and 7 dpi and one day prior to Ad5-pIFN-α administration (Table 6). Results are shown in FIGS. 14-20.

As in the previous experiment, individual groups were housed in separate rooms and animals were monitored clinically for signs of adverse reaction to IFN administration, such as fever and lethargy, and for antiviral activity in the plasma. After FMDV challenge, animals were monitored for 14 days for signs of disease, including temperature and lesions, as well as serologically for viremia, induction of FMDV-specific antibodies and antiviral activity.

TABLE 6

Experimental Design: Duration of Protection

| Group | Animal Number | Inoculum[a] | Day Inoculated | Challenge[b] |
|---|---|---|---|---|
| #1 Control | 61-6, 66-11, 69-11 | $10^9$ pfu Ad5-VSVG | 7 days prechallenge | $3 \times 10^5$ $BID_{50}$ |
| #2 IFN-α | 70-4, 70-5, 70-6 | $10^9$ pfu Ad5-pIFNα7.6.3 | 7 days prechallenge | $3 \times 10^5$ $BID_{50}$ |
| #3 IFN-α | 70-7, 70-8, 71-4 | $10^9$ pfu Ad5-pIFNα7.6.3 | 5 days prechallenge | $3 \times 10^5$ $BID_{50}$ |
| #4 IFN-α | 337-3, 338-6, 342-6 | $10^9$ pfu Ad5-pIFNα7.6.3 | 3 days prechallenge | $3 \times 10^5$ $BID_{50}$ |
| #5 IFN-α | 333-4, 335-9, 335-11 | $10^9$ pfu Ad5-pIFNα7.6.3 | 1 day prechallenge | $3 \times 10^5$ $BID_{50}$ |
| #6 IFN-α | 81-6, 81-10, 308-9 | $10^9$ pfu Ad5-pIFNα7.6.3 | 1 day postchallenge | $3 \times 10^5$ $BID_{50}$ |

[a]Pigs inoculated IM with indicated dose of Ad5-vector
[b]Groups were challenged 7 days (#1 and #2), 5 days (#3), 3 days (#4), 1 day (#5) after administration of Ad5-vector or 1 day before (#6) administration of the Ad5-vector by inoculation in the heel bulb of the left front foot with the indicated dose of FMDV A24

Figure 17:
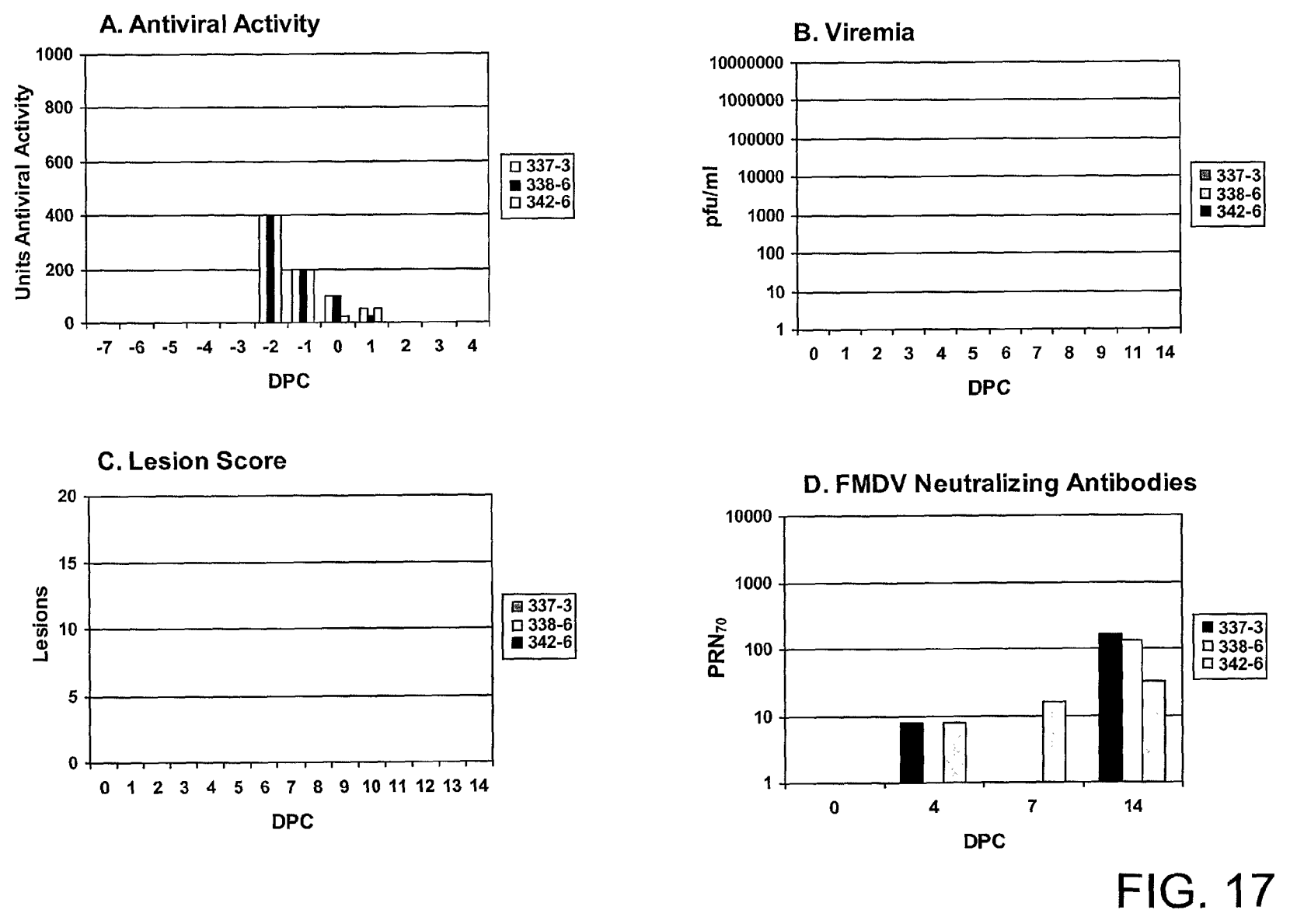
Figure 18:
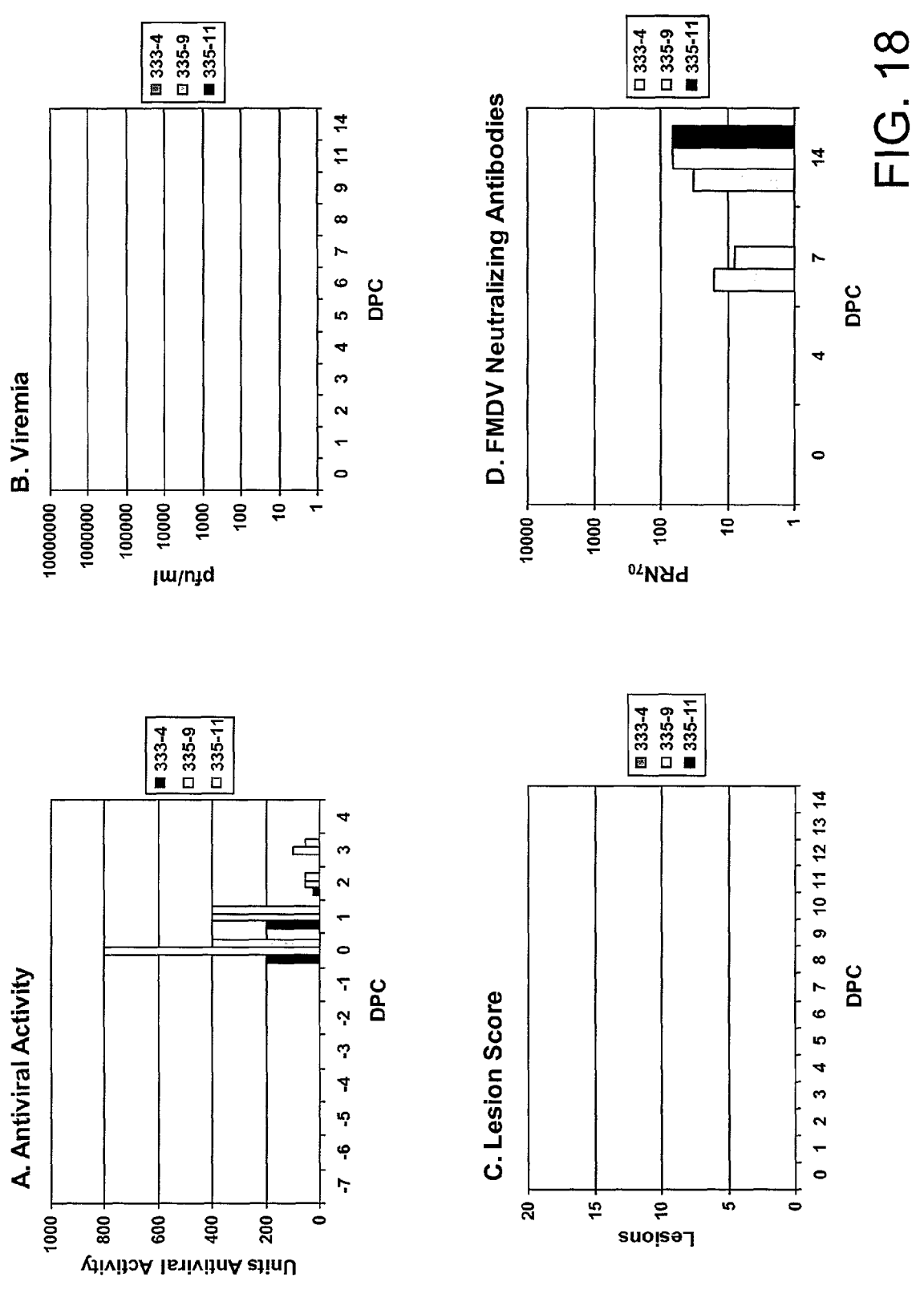
Figure 19:
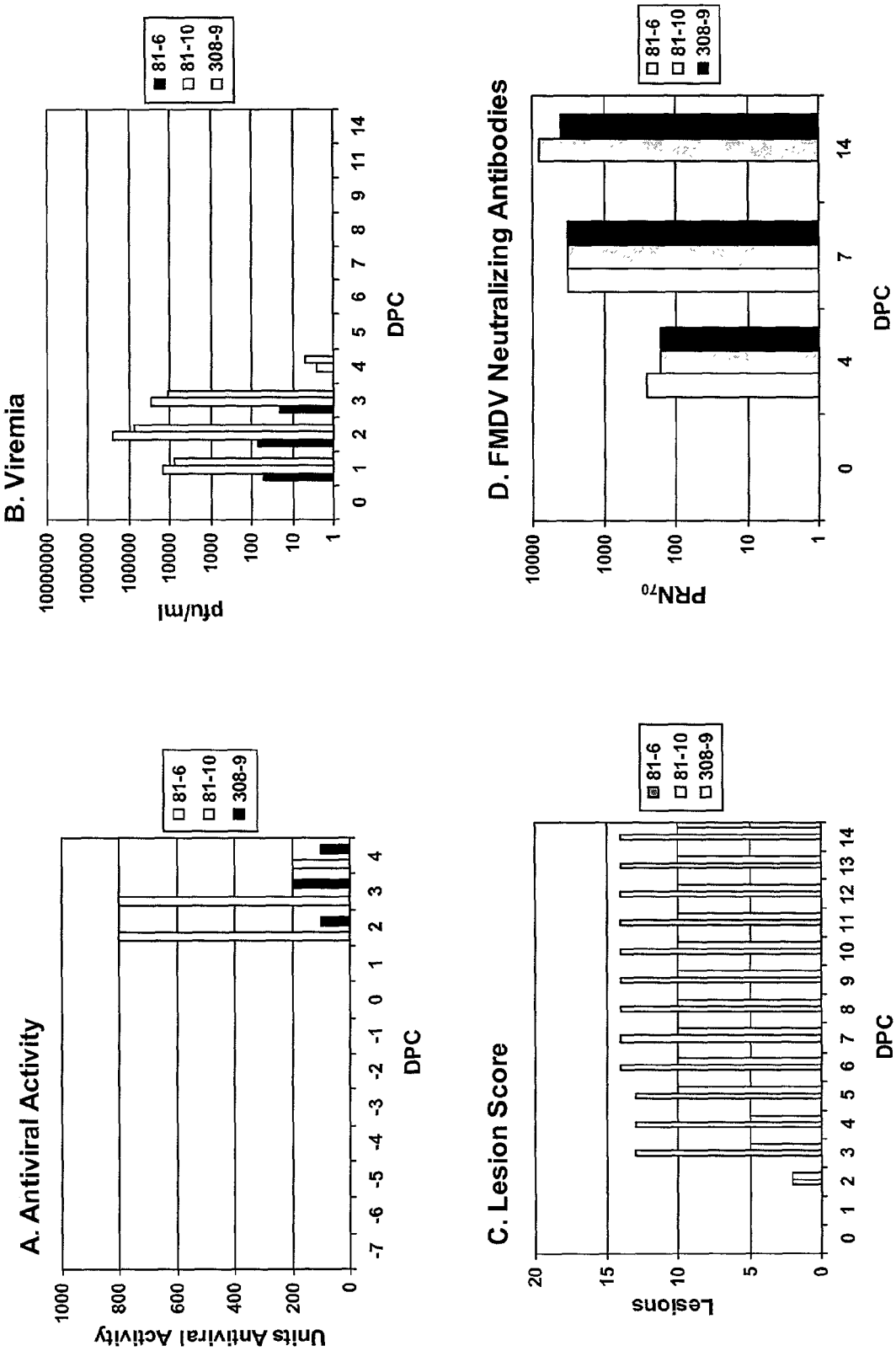
FIG. 19 shows the effect of Ad5-pIFN-α inoculation on protection of swine from FMDV challenge in Group 2 (administration 1 day postchallenge). Effects are determined by antiviral activity, viremia, lesions scored and FMDV neutralizing antibodies produced.

In determining antiviral response prechallenge, it was found that all animals inoculated with Ad5-pIFNα had high levels of antiviral activity, i.e. 200-800 units/ml, one day later (FIGS. 14-19, Panels A). The activity declined by the second day, but generally remained above 100 units/ml for an additional two days. Antiviral activity could be detected for 3-5 days postinoculation. Generally, the Ad5-pIFN-α inoculated animals did not develop elevated temperatures except for Group 2, which had fever for 5-6 days postinoculation (data not shown). In the group given Ad5-pIFN-α 1 day after direct inoculation with virulent FMDV (Group #6), #81-6 and 308-9 had detectable levels of antiviral activity while #81-10 did not (FIG. 19, Panel A). Some of the animals developed fever after Ad5-pIFN-α inoculation (#70-4 and 70-5 in Group 2, #71-4 in Group 3) and appeared somewhat lethargic, but these signs lasted for only 1-2 days.

For viremia and clinical response after challenge, all 3 animals in the control group developed viremia 1 dpc and lesions on day 2 (FIG. 14, Panels B and C). Viremia was detectable for 4 days and reached titers of $9 \times 10^5$ to $3.1 \times 10^7$ pfu/ml. By day 3 all animals in the control group had severe clinical disease. Animal #69-8 developed fever for 3 consecutive days, while the other 2 animals in this group only developed a fever for 1 day. Control animal #61-6 died 5 dpc while #69-8 died 8 dpc. The histopathology findings upon necropsy indicated that both #61-6 and #69-8 had cardiac lesions typical of FMD and that the cause of death for both animals was most likely due to myocardial necrosis.

Figure 15:
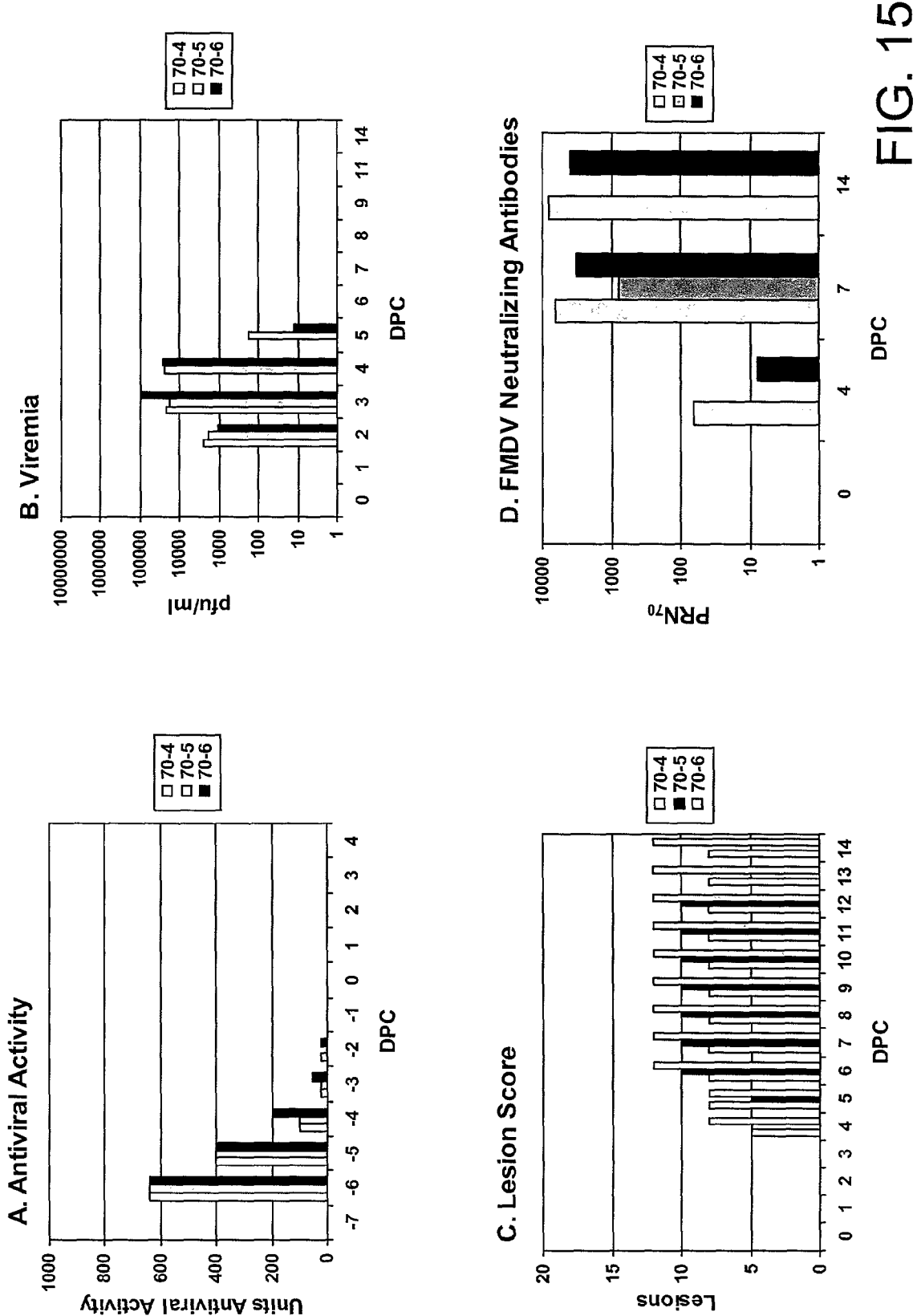
FIG. 15 shows the effect of Ad5-pIFN-α inoculation on protection of swine from FMDV challenge in Group 2 (administration 7 days prechallenge). Effects are determined by antiviral activity, viremia, lesions scored and FMDV neutralizing antibodies produced.

The group given Ad5-pIFN-α 7 days prior to challenge did not have detectable circulating antiviral activity on the day of challenge (FIG. 15, Panel A). This group had viremia at 2 dpc, one day later than the control group (FIG. 15, Panel B). Virus titers ranged from $1.9 \times 10^4$ to $9.1 \times 10^4$ pfu/ml, 1 to 3 logs lower than the control group. Two of the three animals in this group developed lesions at 4 dpc, while the third animal developed lesions on day 5 (FIG. 15, Panel C). All animals in this group developed a fever for 1-2 days. Animal #70-5 died at 12 dpc. The histopathology report found brain stem, thyroid and lung abscesses and the most likely cause of death was due to the brain abscess and brain swelling not related to FMD.

Figure 16:
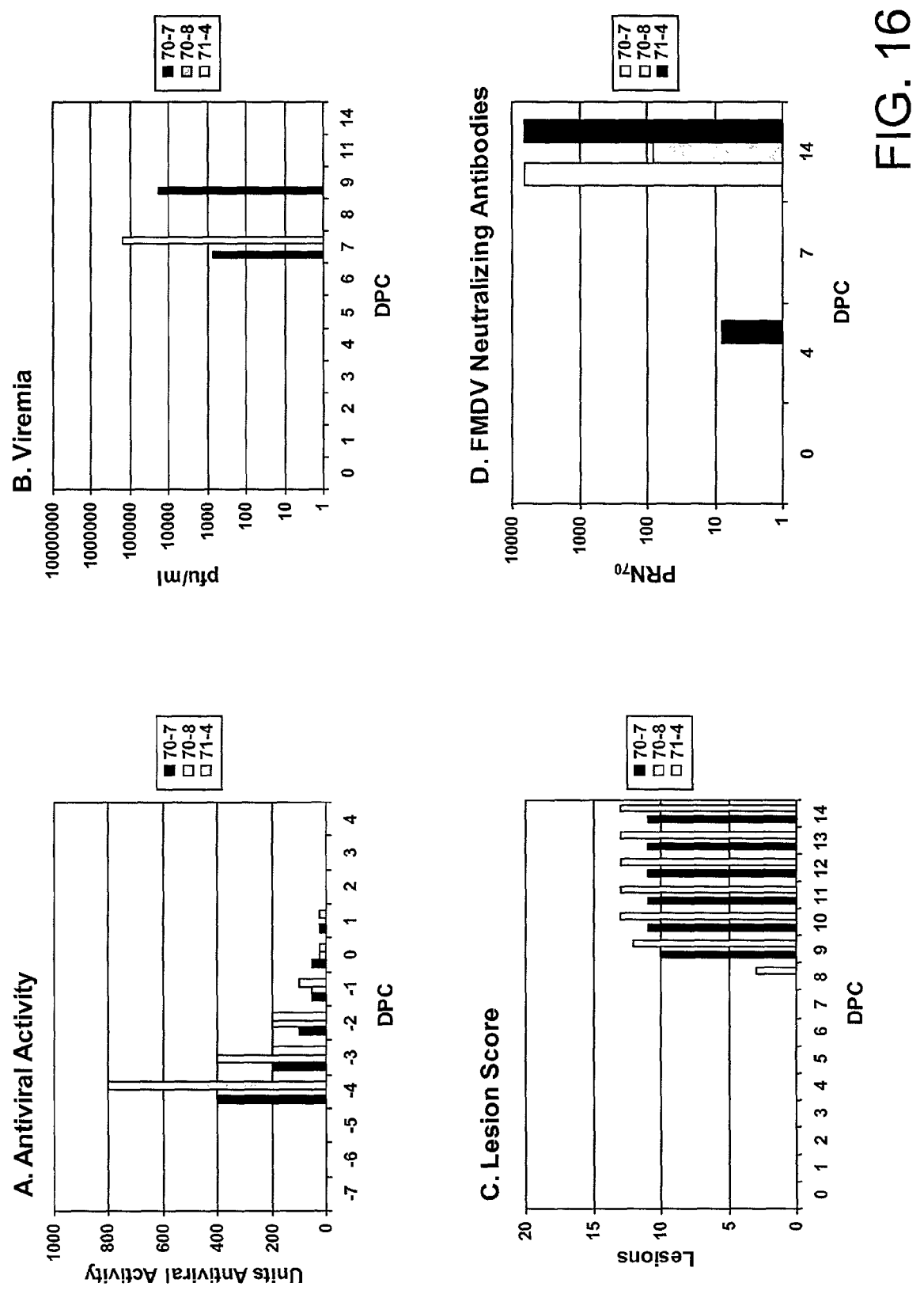

All animals in Groups #3, given Ad5-pIFN-α 5 days prior to challenge, had low but detectable levels of antiviral activity on the day of challenge, 25-50 units/ml (FIG. 16, Panel A). Animal #70-7 developed viremia 7 dpc and lesions 9 dpc (FIG. 16, Panels B and C). Animal #71-4 developed viremia 7 dpc and lesions 8 dpc. Animals #71-4 and #70-7 were moved to separate rooms after lesions developed at 8 and 9 dpc, respectively. Animal #70-8 never developed viremia or lesions even though it was exposed by contact for at least 2 days with clinically ill animals.

All animals in Groups #4 and #5, given Ad5-pIFN-α 3 days and 1 day prior to challenge, respectively had antiviral activity on the day of challenge (FIGS. 17 and 18, Panels A). Activity was still detectable in Group #4 animals one day after challenge, while Group #5 had detectable activity for 2 days after challenge. None of the animals in either of these groups had detectable viremia, even after 3 blind passages of blood in BHK cells, or developed any clinical signs of disease (FIGS. 17 and 18, Panels B and C).

All animals in Group #6, given Ad5-pIFN-α 1 dpc, developed viremia 1 day later (FIG. 19, Panel B). However, the maximum virus titer of #81-6 was only $7 \times 10^1$ pfu/ml. This animal never developed clinical signs of disease even though it was exposed, by contact, for at least 7 days to two actively infected animals. However, #81-6 died on day 9 postchallenge. The histopathology report revealed severe bacterial meningitis, and death was most likely due to bacterial meningitis disseminating through the blood from skin abscesses not related to FMD.

Figure 20:
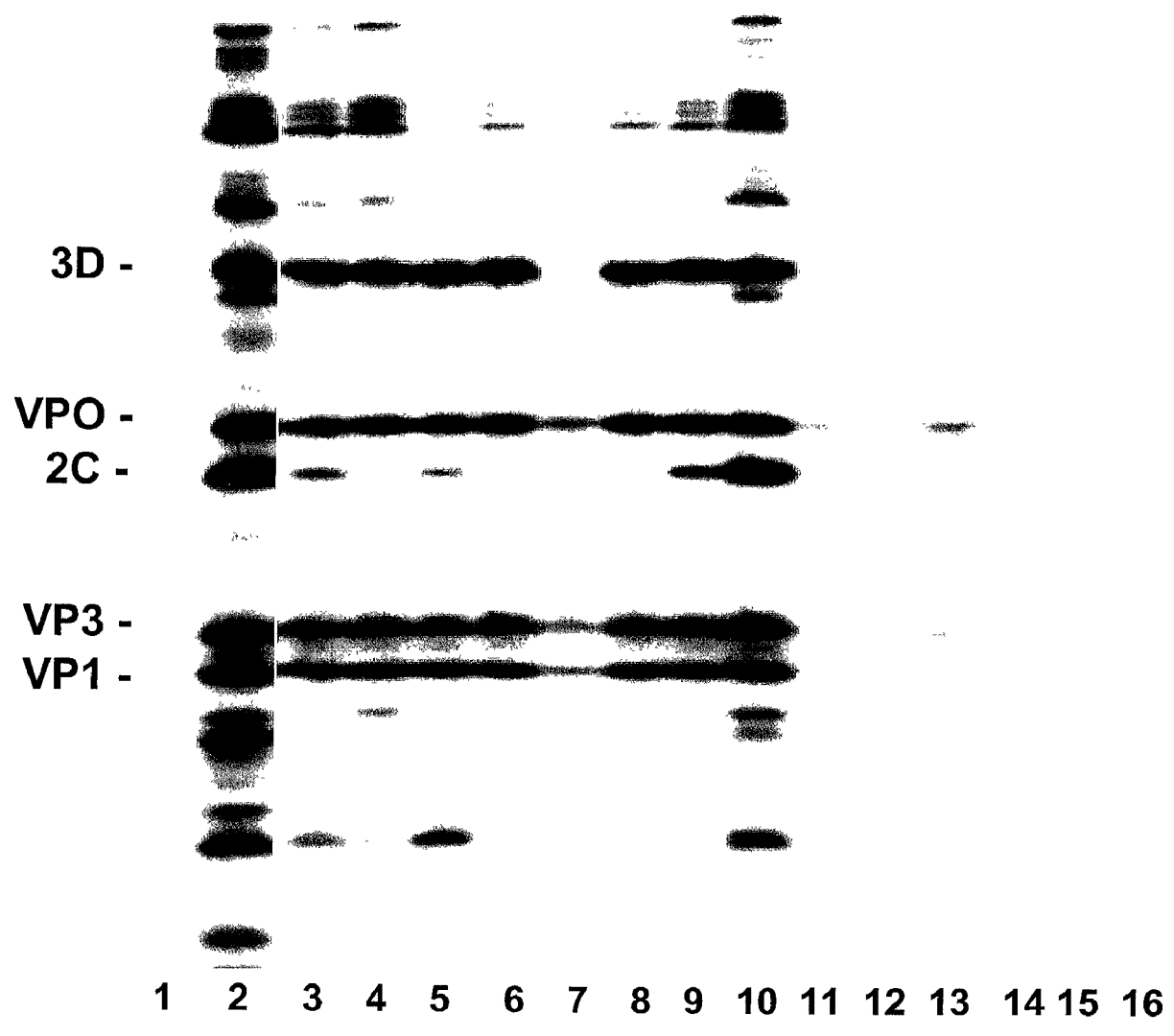

For the serological response, sera from all animals were assayed for an FMDV-specific neutralizing antibody response, and 14 dpc sera was assayed for the induction of antibodies against viral NS proteins. All surviving animals in Groups 1 and 2 had a significant FMDV-specific neutralizing antibody response (FIGS. 14 and 15) and developed antibodies against viral NS proteins (FIG. 20, lanes 3-5). The 2 clinically ill animals in Group 3 developed antibodies against viral NS proteins (FIG. 20, lanes 6 and 8), while the animal in the group that had not developed clinical disease or viremia, #70-8, only had antibodies against viral structural proteins and not NS proteins (FIG. 20, lane 7). The animals in Groups 4 and 5, which were all protected from clinical disease and had no viremia, had low levels of antibodies against viral structural proteins and no detectable antibodies against NS proteins (FIG. 20, lanes 11-16). In support of these results, the sera from animals in Groups 4 and 5 were negative in the 3 ABC ELISA These results demonstrate that these animals were protected against virus replication. The surviving animals in Group 6 developed a significant FMDV-specific neutralizing antibody response (FIG. 19) and developed antibodies against viral NS proteins (FIG. 20, lanes 9 and 10).

Example 10

Protection of Swine Co-Administered Ad5-pIFN-α and Ad5-A24 from Infection with FMDV.

In the experiment described in Example 9, swine could be protected from FMD when given Ad5-pIFN-α 1 or 3 days prior to challenge. Since swine inoculated with Ad5-pIFN-α 5 days prior to challenge were either completely protected, #70-8, or developed viremia and clinical disease 6-7 days later than the control group, the potential of dual inoculation of swine with Ad5-pIFN-α and Ad5-FMD was investigated as a method of very rapidly inducing a non-specific protective antiviral effect prior to the onset of the adaptive immune response against the specific FMDV serotype used in the vaccine.

It has been demonstrated that Ad5-FMDV vectors containing the capsid (P1) and 3C proteinase coding regions of FMDV can protect swine challenged with virulent FMDV (Mayr et al. 1999. *Virology*. vol. 2263, pp. 496-506; Mayr et al. 2001. *Vaccine*. vol. 19, pp. 2152-2162; Moraes et al. 2002. *Vaccine*. vol. 20, pp. 1631-1639). Therefore, an Ad5-FMDV vector containing the P1 coding region of A24 Cruziero, a field strain from Brazil (Ad5-A24), was used. Swine given one inoculation of this vector are protected as early as 7 days later from direct inoculation challenge with homologous virus (Moraes et al., 2002, supra).

In this experiment, groups were inoculated with Ad5-VSVG (Group 1), Ad5-A24 (Group 2), Ad5-pIFN-α (Group 3) and Ad5-A24 plus Ad5-pIFN-α (Group 4) (Table 7). Animals were challenged 5 days later by footpad inoculation with $3.5 \times 10^5$ BIC$_{50}$ FMDV A24. Plasma, serum, and whole blood samples were collected and assayed as in Example 9. In addition, nasal swabs were assayed to monitor virus shedding. Animals were also monitored clinically throughout the course of the experiment. Results are shown in FIGS. 21-25.

TABLE 7

Experimental Design: Effect of Ad5-pIFNα and Ad5-A24.

| Group | Animal Number | Inoculum[a] | Challenge[b] |
|---|---|---|---|
| #1 Ad5-VSVG | 9987-9989 | $10^9$ pfu | $3 \times 10^5$ BID$_{50}$ |
| #2 Ad5-A24 | 9981-9983 | $5 \times 10^9$ pfu | $3 \times 10^5$ BID$_{50}$ |
| #3 Ad5-pIFNα7.6.3 | 9975-9977 | $10^9$ pfu | $3 \times 10_5$ BID$_{50}$ |
| #4 Ad5-pIFNα7.6.3 + Ad5-A24 | 9972-9974 | $6 \times 10^9$ pfu | $3 \times 10^5$ BID$_{50}$ |

[a]Pigs inoculated IM with indicated dose of Ad5-vector
[b]Pigs challenged 5 days after administration of Ad5-vector by inoculation in the heel bulb of the left front foot with the indicated dose of FMDV A24

Figure 21:
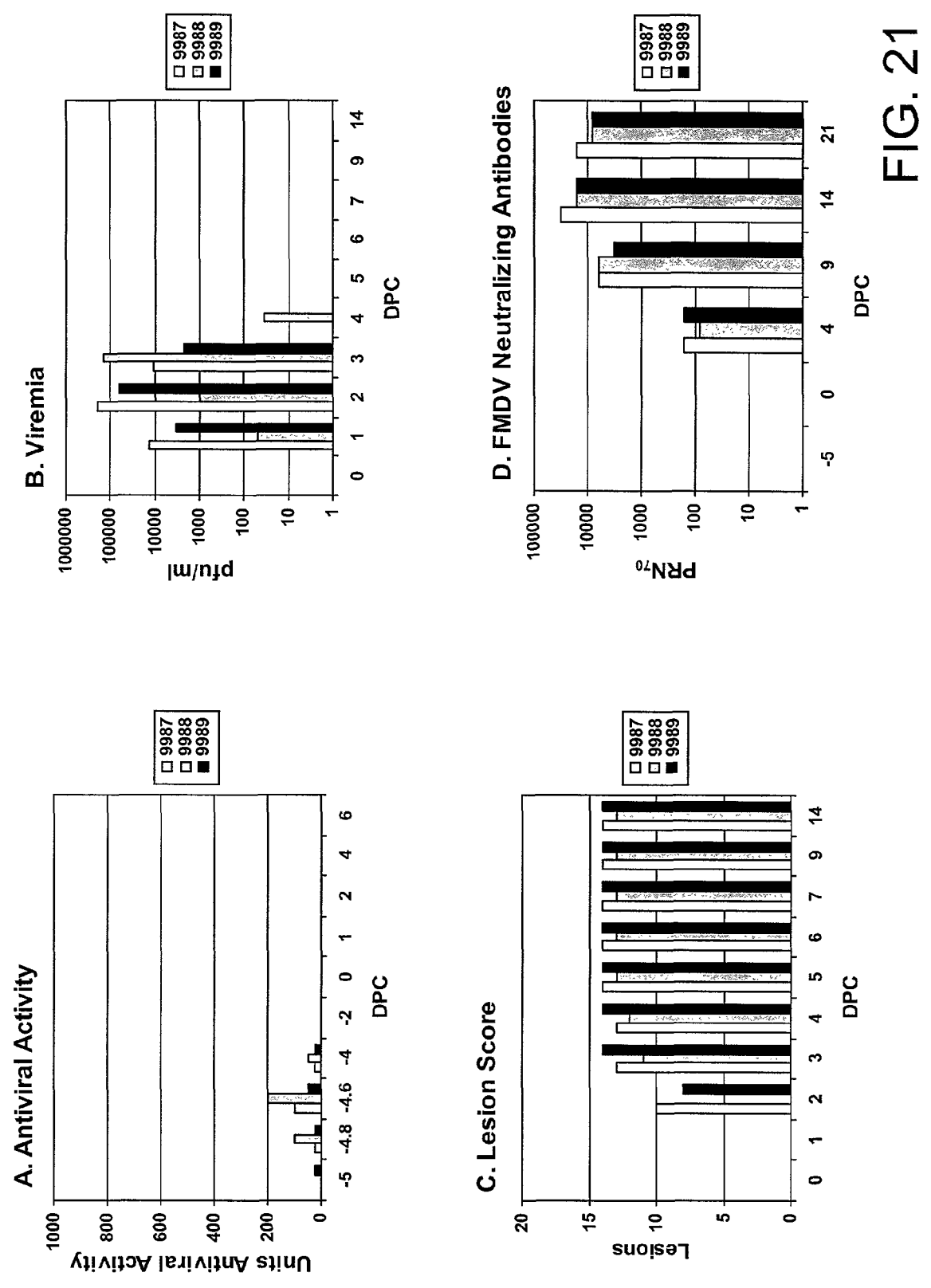
Figure 22:
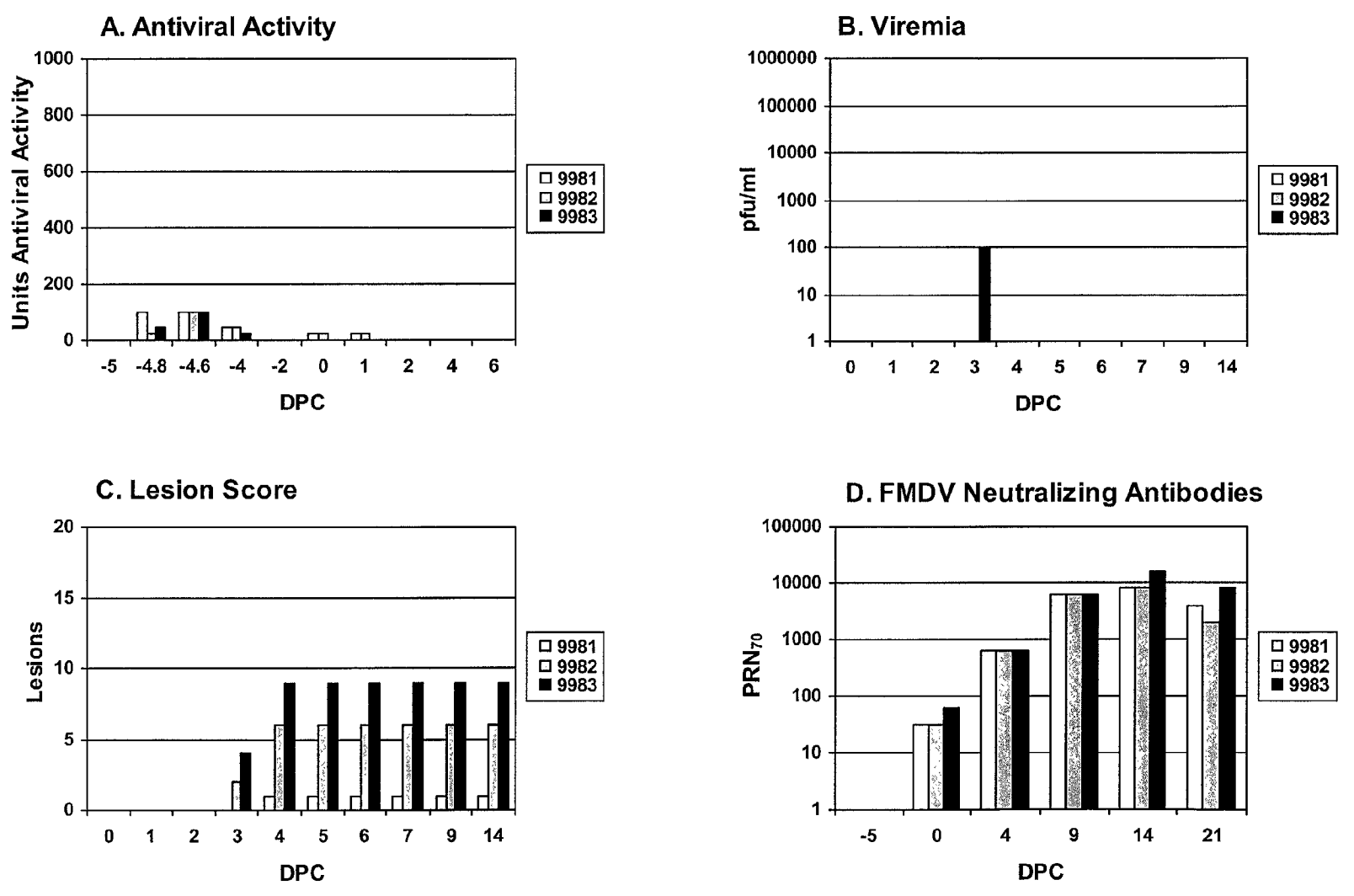
Figure 23:
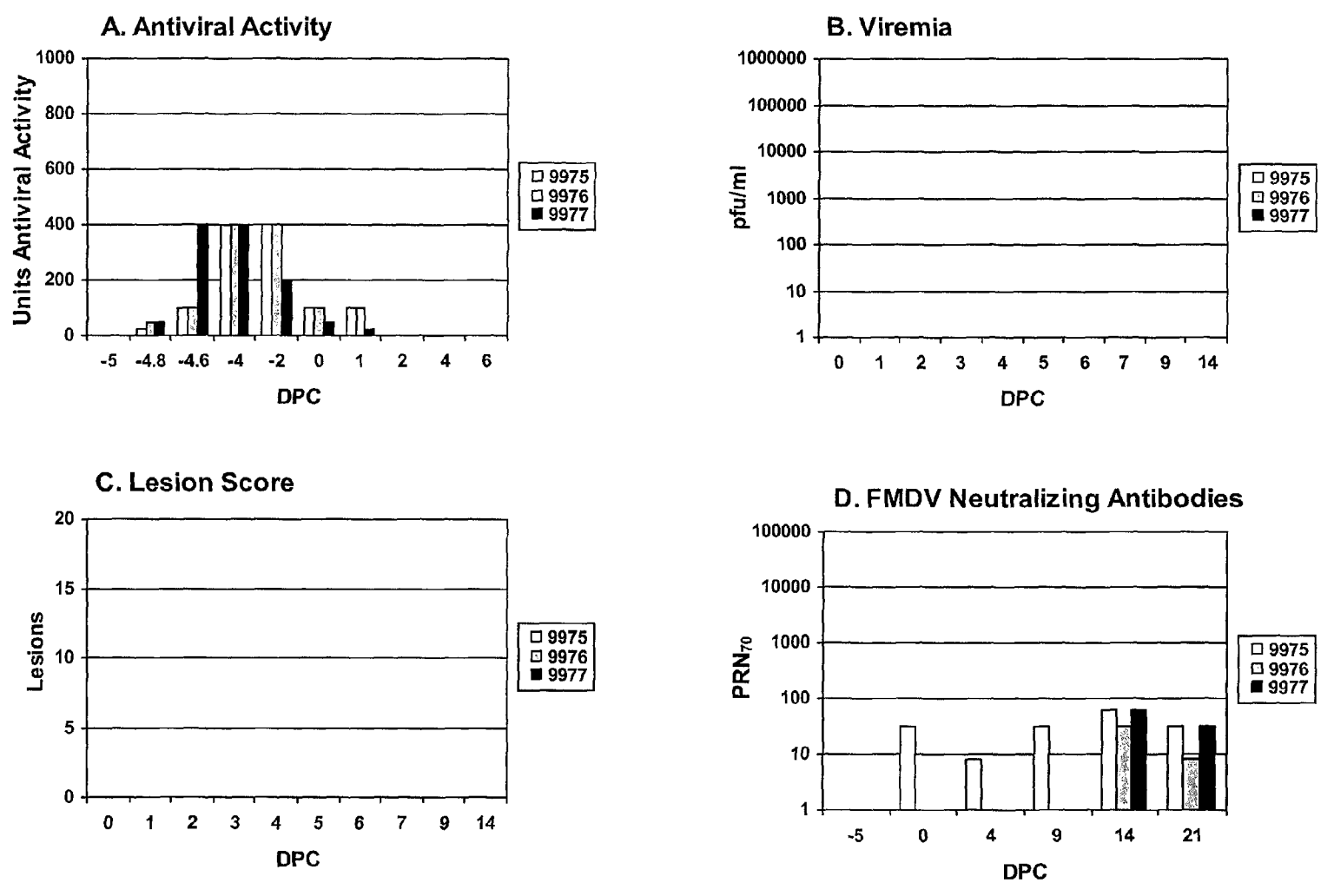
Figure 24:
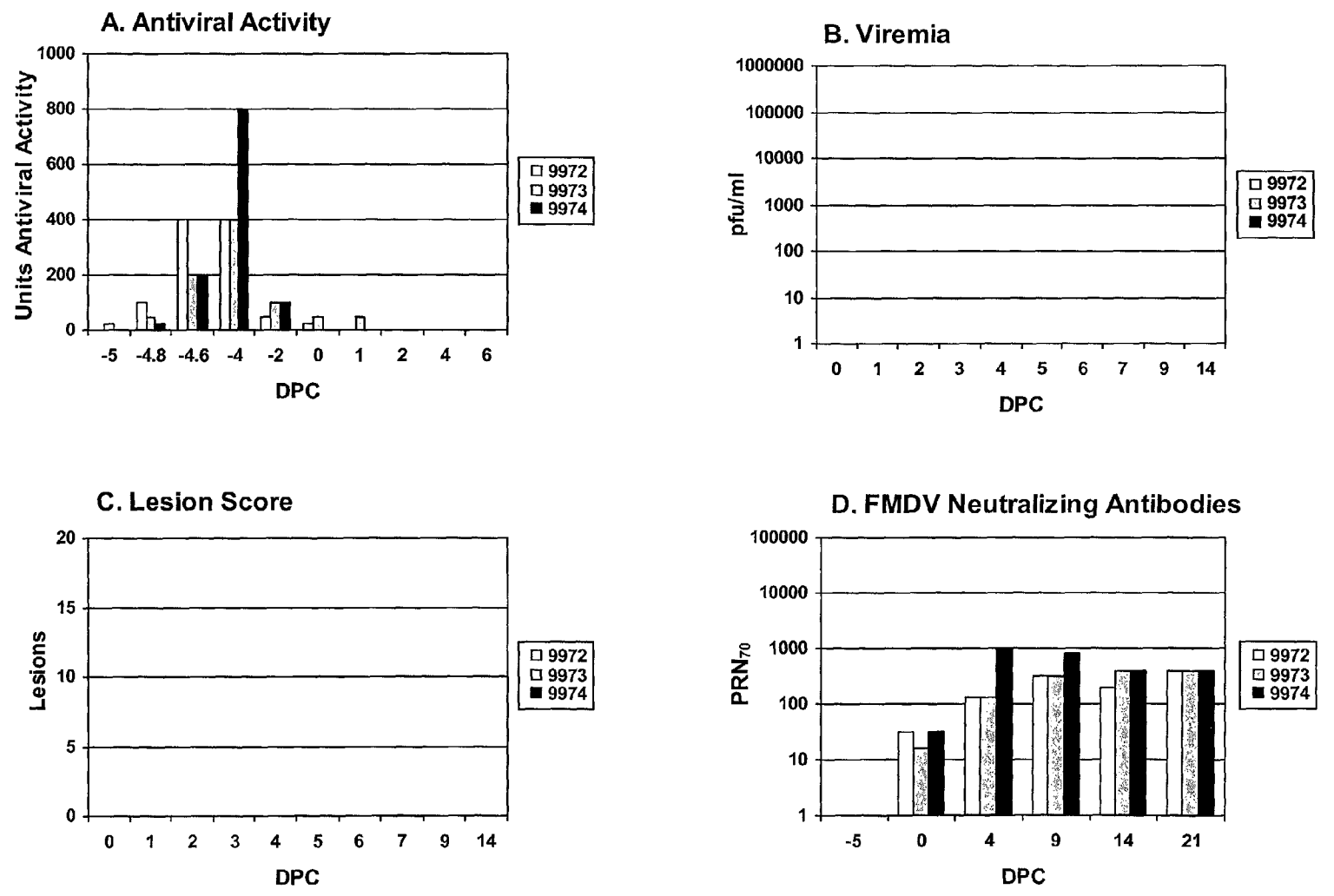

To determine antiviral response prechallenge, plasma was obtained at various times post inoculation. All animals in groups inoculated with Ad5-pIFN-α (Groups 3 and 4) developed an antiviral response as early as 4 hpi (−4.8) that lasted for approximately 4-5 days (FIGS. 23 and 24). The maximal activity was 400-800 units/ml. Groups 1 and 2 given the Ad5 vector without the IFN-α gene also developed an antiviral response by 4 hpi (−4.8), but this only lasted for approximately 1 day (FIGS. 21 and 22). Group 2 and Group 4 received 5-fold and 6-fold more virus, respectively, than Group 3, (Table 7).

Viremia and the clinical response after challenge were also determined. All 3 animals in Group 1 (control) developed high levels of viremia at 1 dpc, low virus titers in nasal swabs, $10^1$-$10^2$ pfu/ml, at 1 dpc that lasted for 2-3 additional days, and lesions at 2 dpc (FIG. 21). All animals developed severe signs of disease. The animals seroconverted by 4 dpc.

In the group given Ad5-A24 (Group 2) only animal #9983 developed a low level of viremia, $10^2$ pfu/ml, for 1 day (FIG. 22). However, all 3 animals in this group had low levels of virus, $10^1$-$10^2$ pfu/ml, in nasal swabs for 1-2 days. Lesions were detectable 3-4 dpc, 1-2 days later than the control group, and were significantly less severe. These animals had a low, but detectable, FMDV-specific neutralizing antibody response on the day of challenge. The titers were significantly boosted by 4 dpc.

The groups given Ad5-pIFN-α alone (Group 3) or in combination with Ad5-A24 (Group 4) were completely protected (FIGS. 23 and 24). Five of the 6 animals in these groups had antiviral activity on the day of challenge. The animals did not develop viremia, had no detectable virus in nasal swabs and had no clinical signs of disease. The animals in Group 4 developed a low, but detectable FMDV-specific neutralizing antibody response at 4 dpi that was significantly boosted by 4 dpc and remained at a high level 21 dpc (FIG. 24).

Figure 25:
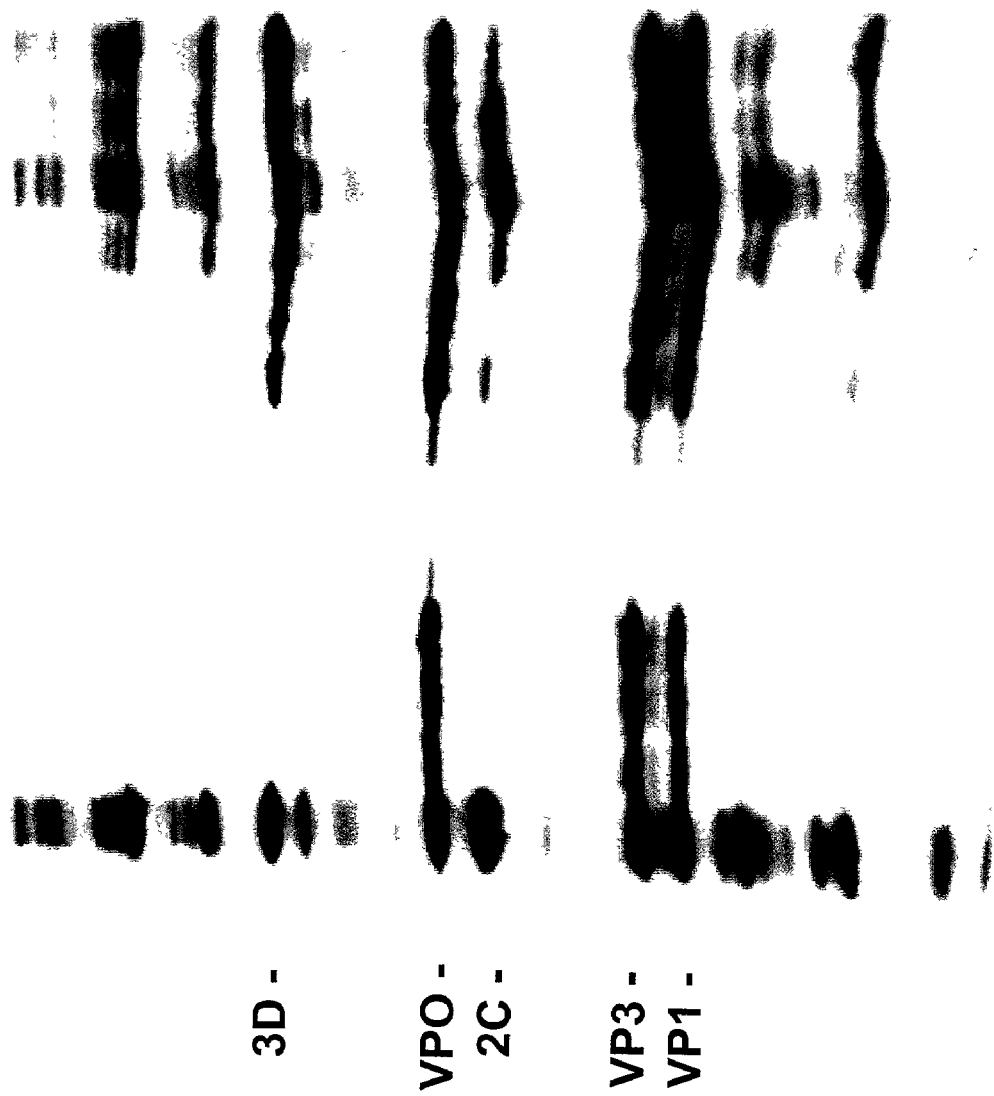
FIG. 25 shows the RIP of 14 dpc sera from swine inoculated with Ad5-pIFN-α, Ad5-A24, or Ad5-pIFN-α and Ad5-A24 and challenged 5 days later.

The serological response was also determined. Fourteen dpc sera were tested for antibodies against viral structural and NS proteins. The animals in Groups 1 and 2, which all developed clinical disease, all had antibodies against both viral structural and NS proteins (FIG. 25, lanes 9-14). In contrast the animals in Groups 3 and 4, none of which developed clinical disease or viremia, only had antibodies against the viral structural proteins (lanes 3-8). Interestingly, the animals in Group 4 which were given both Ad5-pIFN-α and Ad5-A24 and had higher levels of FMDV-specific neutralizing antibodies than the animals in Group 3 (FIGS. 23 and 24), which were inoculated with only Ad5-pIFN-α, also had higher levels of antibodies against the viral structural proteins (FIG. 25, lanes 3-5 [inoculated with both vectors], lanes 6-8 [inoculated only with Ad5-pIFN-α]). In support of these results, the sera from animals in Groups 3 and 4 were all negative in the 3 ABC ELISA.

Example 11

Expression of Ad5-bIFN-α and Ad5-bIFN-β in Cattle.

A dose-response experiment was performed in cattle inoculated with Ad5-bIFN-α and Ad5-bIFN-β. Cattle (one animal per dose) were inoculated IM with 1, 2.5 or $5 \times 10^9$ pfu of each virus. As a control an additional animal was inoculated with $5 \times 10^9$ pfu Ad5-VSVG. Animals were monitored for adverse clinical effects of IFN administration, and temperatures taken daily. Plasma samples were taken daily for 7 days and assayed for antiviral activity, and serum samples were taken at 0 and 13 dpi for analysis of Ad5-specific neutralizing antibody response.

None of the animals displayed abnormal behavior or had elevated temperatures. No antiviral response was detectable in any of the animals inoculated with the viruses. All animals developed a significant Ad5-specific neutralizing antibody response at 13 dpi indicating that these animals were exposed to the recombinant viruses.

There are a number of possibilities to explain the lack of detectable antiviral activity in cattle, including size difference between the swine and cattle used in the experiments (35-40 lbs vs 400-450 lbs), low level of expression of bIFNs in cattle as compared to pIFNs in swine, and less efficient infection of cattle compared to swine with human Ad5 viruses.

Example 12

Expression of Ad5-pIFN-α and Ad5-pIFN-β in Cattle and Swine.

It has been shown that pIFN-α and pIFN-β are biologically active in bovine cell cultures (Chinsangaram et al., 2001, supra, Table 3). Therefore, swine and cattle were inoculated with different doses of these viruses, the animals monitored and plasma samples obtained daily for 7 dpi (Table 8).

The swine inoculated with either dose of Ad5-pIFN-α developed fever for 1-2 days. The high-dose inoculated animal was also lethargic and did not eat well. All of the other inoculated swine or cattle behaved normally and did not develop fever.

The swine given the low dose of Ad5-pIFN-α developed an antiviral response by 1 dpi and this lasted for an additional 3 days (Table 8). The swine inoculated with the high dose of Ad5-pIFN-α developed a higher antiviral response by 1 dpi which continued for an additional 4 days. Only the swine given the high dose of Ad5-pIFN-β developed an antiviral response. The induced antiviral activity in this animal was significantly lower than in the high-dose Ad5-pIFN-α inoculated animal and only lasted for 2 days. The lower levels of antiviral activity induced in Ad5-pIFN-β infected swine as compared to Ad5-pIFN-α infected swine may be related to the lower levels of expression of pIFN-β versus pIFN-α in infected IBRS2 cells (see Example 5).

Only the bovine inoculated with the high dose of Ad5-pIFN-α developed an antiviral response. This response was significantly lower than found in the identically inoculated swine and only lasted for 1 day. These results suggest that the effectiveness of IFN treatment is related to the dose of the inoculum and the size of the inoculated animals. It is also possible that the binding of human Ad5 viruses is more efficient in swine than in cattle.

Example 13

Expression of Ad5-bIFN-α and Ad5-bIFN-β.

It was previously shown that bIFN-α is biologically active in both bovine and swine cells cultures, while bIFN-β only has biological activity in bovine cell lines (Chinsangaram et al., 2001 supra, Table 4). To determine if Ad5-bIFN could induce an antiviral response swine, swine were inoculated with different doses of these viruses (Table 9). The animals were monitored and plasma samples assayed for an antiviral response in the appropriate cell lines.

The swine inoculated with 1 or $5 \times 10^9$ pfu Ad5-bIFN-α both developed an antiviral response by 1 dpi. The animal inoculated with the higher dose had higher activity, but in each case the antiviral activity was only detectable for 1 day. The swine inoculated with 1 or $5 \times 10^9$ pfu Ad5-bIFN-β both developed antiviral activity by 1 dpi. The low dose inoculated animal had detectable activity for 3 additional days, while the high dose inoculated animal had activity for 4 additional days.

TABLE 8

Experimental Design: Dose-Response of Ad5-pIFN-α and Ad5-pIFN-β in Swine and Cattle.

| Inoculum[a] | Dose | Species | Antiviral Activity[b] | | | | | | | |
|---|---|---|---|---|---|---|---|---|---|---|
| | | | 0 dpi | 1 dpi | 2 dpi | 3 dpi | 4 dpi | 5 dpi | 6 dpi | 7 dpi |
| Ad5-VSVG | $5 \times 10^9$ pfu | Swine | <25 | <25 | <25 | <25 | <25 | <25 | ND[c] | ND |
|  |  | Bovine | <25 | <25 | <25 | <25 | <25 | <25 | ND | ND |
| Ad5-pIFNα7.6.3 | $1 \times 10^9$ pfu | Swine | <25 | 400 | 200 | 100 | 25 | <25 | ND | ND |
|  | $5 \times 10^9$ pfu |  | <25 | 800 | 800 | 400 | 100 | 25 | 25 | <25 |
|  | $1 \times 10^9$ pfu | Bovine | <25 | <25 | <25 | <25 | <25 | <25 | ND | ND |
|  | $5 \times 10^9$ pfu |  | <25 | 50 | <25 | <25 | <25 | <25 | ND | ND |
| Ad5-pIFNβ1.4.6 | $1 \times 10^9$ pfu | Swine | <25 | <25 | <25 | <25 | <25 | <25 | ND | ND |
|  | $5 \times 10^9$ pfu |  | <25 | 200 | 100 | <25 | 25 | <25 | ND | ND |
|  | $1 \times 10^9$ pfu | Bovine | <25 | <25 | <25 | <25 | <25 | <25 | ND | ND |
|  | $5 \times 10^9$ pfu |  | <25 | <25 | <25 | <25 | <25 | <25 | ND | ND |

[a]Animals were inoculated IM in the neck with 1 ml of the indicated dose of Ad5-vector
[b]Highest dilution that reduced FMDV A12 plaque number by 50% in IBRS2 cells
[c]Not done

TABLE 9

Experimental Design: Dose-Response of Ad5-bIFN-α and Ad5-bIFN-β in Swine

| Inoculum[a] | Dose | Antiviral Activity[b] | | | | | | | |
|---|---|---|---|---|---|---|---|---|---|
| | | 0 dpi | 1 dpi | 2 dpi | 3 dpi | 4 dpi | 5 dpi | 6 dpi | 7 dpi |
| Ad5-Blue | $5 \times 10^9$ pfu | <25 | <25 | <25 | <25 | <25 | <25 | ND[c] | ND |
| Ad5-bIFNα 9.2.2 | $1 \times 10^9$ pfu | <25 | 50 | <25 | <25 | <25 | <25 | ND | ND |
| | $5 \times 10^9$ pfu | <25 | 100 | <25 | <25 | <25 | <25 | ND | ND |
| Ad5-bIFNβ 5.3.1 | $1 \times 10^9$ pfu | 25 | 400 | 200 | 50 | 25 | <25 | ND | ND |
| | $1 \times 10^9$ pfu | <25 | 400 | 200 | 50 | 50 | 25 | ND | ND |

[a] Animals were inoculated IM in the neck with 1 ml of the indicated dose of Ad5-vector
[b] Highest dilution that reduced FMDV A12 plaque number in IBRS2 cells by 50% in animals inoculated with Ad5-bIFN-α or highest dilution that reduced VSV-NJ plaque number in MDBK cells by 50% in animals inoculated with Ads-bIFN-β
[c] Not done

Example 14

Protection of Bovines Inoculated with Ad5-pIFN-α from Infection with FMDV.

pIFN-α is biologically active in bovine cells (Table 3) and administration of Ad5-pIFN-α induces a low level of antiviral activity in bovines (Table 8). To determine if Ad5-pIFN-α can protect cattle from challenge with cattle-passaged FMDV, cattle weighing approximately 200 lbs were inoculated with a very high dose of Ad5-pIFN-α, i.e. $1 \times 10^{10}$ pfu per animal (Table 10). In group 1 cattle were inoculated IM with a control virus, Ad5-Blue, in Groups 2 and 3 IM with Ad5-pIFN-α. All animals were challenged intradermally in the tongue with $2 \times 10^4$ BID$_{50}$ cattle-passaged A24. Animals in Groups 1 and 2 were challenged 1 dpi, while the animals in Group 3 were challenged 2 dpi. Animals were monitored every other day for clinical signs of disease. Temperatures were taken daily, blood samples and nasal swabs daily up to 8 dpc and serum samples at 1, 4, 7 and 14 dpc.

TABLE 10

Experimental Design: Effect of Ad5-pIFN-α

| Group | Animal Number | Inoculum[a] | Day of Challenge | Challenge[b] |
|---|---|---|---|---|
| #1 Ad5-Blue | 8-10 | $10^{10}$ pfu | 1 dpi | $2 \times 10^4$ BID$_{50}$ |
| #2 Ad5-pIFNα7.6.3 | 11-13 | $10^{10}$ pfu | 1 dpi | $2 \times 10^4$ BID$_{50}$ |
| #3 Ad5-pIFNα7.6.3 | 14-16 | $10^{10}$ pfu | 2 dpi | $2 \times 10^4$ BID$_{50}$ |

[a] Cattle inoculated IM with indicated dose of Ad5-vector
[b] Cattle challenged 1 or 2 days after administration of Ad5-vector by intradermal inoculation in the tongue with the indicated dose of bovine passaged FMDV A24 Cruziero The animals in Groups 2 and 3 developed an antiviral response of between 50-200 units/ml beginning at 1 dpi and lasting for an additinal 1-2 days. As expected, the Ad5-Blue inoculated animals had no detectable antiviral activity. Only the animals in Groups 2 and 3 developed a fever for 1-2 days that then returned to normal, but otherwise these animals appeared healthy.

All the Ad5-Blue inoculated animals developed low-level viremia 1 dpc which increased and continued for an additional 1-3 days. Virus was detectable in nasal swabs in all animals 2-3 dpc. On day 2 postchallenge the animals had vesicles on the tongue at sites distinct from the challenge sites and on the feet. Subsequently some of the animals had vesicles on the gums and snout and vesicles on all four feet (FIG. 26).

Viremia was delayed until 2 dpc in the animals in Groups 2 and 3 and continued for an additional 2 days. Virus was detectable in nasal swabs of all animals 2-3 dpc. The appearance of vesicles in Group 2 was delayed until 4 dpc and disease was not as severe as in the control group (FIG. 26). In Group 3, animal #16 never developed vesicles, while the appearance of vesicles in the other two animals in this group was delayed and disease was not as severe as in the control group (FIG. 26).

Cattle inoculated with Ad5-pIFN-α 1 (Group 2) or 2 days (Group 3 prior to challenge with virulent FMDV were partially protected from clinical disease. One Ad5-pIFN-α-inoculated animal never developed clinical disease, while in the remaining animals, the appearance of vesicles was delayed and disease was less severe than in control Ad5-Blue-inoculated animals. Similarly, although all the Ad5-pIFN-α-inoculated animals developed viremia, it was delayed for 1 day as compared to the control group.

We claim:

1. An early-acting effective anti-foot-and mouth disease virus vaccine suitable for administering intramuscularly to animals, said vaccine comprising an effective amount of: a nucleic acid construct which is a DNA sequence which is capable of expressing an interferon-α protein of cloven-hooved animal origin and/or an interferon-β protein of porcine origin in animals susceptible to foot and mouth disease, and an additional nucleic acid construct which is a DNA sequence which encodes all the viral structural proteins and the 3C proteinase of a foot and mouth disease virus (FMDV) and which is capable of expressing said structural proteins and 3C proteinase in animals susceptible to foot and mouth disease, wherein said structural proteins stimulate an immune response when administered to said animals, and wherein said interferon-α and/or interferon-β protein is expressed prior to development of specific immunity to said structural proteins and 3C proteinase.

2. The vaccine of claim 1 wherein the animals susceptible to foot and mouth disease are swine, cattle, or sheep.

3. An early-acting effective anti-FMDV vaccine suitable for administering to animals, said vaccine comprising an effective amount of: a viral gene transfer vector wherein said vector is an adenovirus and wherein said vector comprises a nucleic acid construct capable of expressing an interferon-α protein of cloven-hooved animal origin and/or an interferon-β protein of porcine origin in animals susceptible to foot and mouth disease, and an additional viral gene transfer vector wherein said vector is an adenovirus and wherein said vector comprises a nucleic acid construct which encodes all the viral structural proteins and the 3C proteinase of a foot and mouth disease virus and which is capable of expressing said structural proteins and 3C proteinase in animals susceptible to foot and mouth disease, wherein said structural proteins stimulate an immune response when administered to said animals, and wherein said interferon-α and/or interferon-β protein is expressed prior to development of specific immunity to said structural proteins and 3C proteinase and has an early-acting anti-FMDV effect.

4. An early-acting effective anti-FMDV vaccine suitable for administering to animals, said vaccine comprising an effective amount of a viral gene transfer vector wherein said vector is an adenovirus and wherein said vector comprises a nucleic acid construct capable of expressing an interferon-α protein of cloven-hooved animal origin and/or an interferon-β protein of porcine origin in animals susceptible to foot and mouth disease, and comprises a nucleic-acid construct which encodes all the viral structural proteins and the 3C proteinase of a foot and mouth disease virus and which is capable of expressing said structural proteins and 3C proteinase in animals susceptible to foot and mouth disease, wherein said structural proteins stimulate an immune response when administered to said animals, and wherein said interferon-α and/or interferon-β protein is expressed prior to development of specific immunity to said structural proteins and 3C proteinase and has an early-acting anti-FMDV effect.

5. An early-acting effective anti-FMDV vaccine suitable for administering to animals, said vaccine comprising an effective amount of: (1) a viral gene transfer vector wherein said vector is an adenovirus and wherein said vector comprises a nucleic acid construct capable of expressing an interferon-α protein of cloven-hooved animal origin and/or an interferon-β protein of porcine origin in animals susceptible to foot and mouth disease, and (2) an effective FMDV vaccine in an amount effective for stimulating an immune response when administered to said animals, and wherein said interferon-α and/or interferon-β protein is expressed prior to development of specific immunity to said effective FMDV vaccine and has an early-acting anti-FMDV effect.

6. The vaccine of any one of claims 3, 4, or 5, wherein the composition is administered intramuscularly, subcutaneously, intradermally, nasally, or intraperitoneally.

7. The vaccine of any one of claims 3, 4, or 5, wherein the animals susceptible to foot and mouth disease are swine, cattle, or sheep.

8. A method for protecting susceptible animals from foot and mouth disease comprising:
administering to said animals an effective dosage of an anti-FMDV vaccine, said vaccine comprising an effective amount of: a viral gene transfer vector wherein said vector is an adenovirus and wherein said vector comprises a nucleic acid construct capable of expressing an interferon-α protein-of-cloven-hooved animal origin and/or an interferon-β protein of porcine origin in animals susceptible to foot and mouth disease, and (2) an effective FMDV vaccine in amount effective for stimulating an immune response when administered to said animals, wherein said interferon-α and/or interferon-β protein is expressed prior to development of specific immunity to said effective FMDV vaccine, wherein said expressed interferon-α and/or interferon-β protein results in an early-acting antiviral effect, inhibiting or delaying onset or severity of said foot and mouth disease when challenged with virulent FMDV within one to seven days post administration, and wherein said effective FMDV vaccine stimulates a protective long term immune response in said animals.

9. The method of claim 8 wherein said animals susceptible to foot and mouth disease are swine, cattle, or sheep.

10. A method for protecting susceptible animal from foot and mouth disease comprising:
administering to said animals an effective dosage of an anti-FMDV vaccine, said vaccine comprising an effective amount of: a first viral gene transfer vector wherein said first vector is an adenovirus and wherein said first vector comprises a nucleic acid construct capable of expressing an interferon-α protein of cloven-hooved animal origin and/or an interferon-β protein of porcine origin in animals susceptible to foot and mouth disease, and a second viral gene transfer vector wherein said second vector is an adenovirus and wherein said second vector comprises a nucleic acid construct which encodes all the viral structural proteins and the 3C proteinase of a foot and mouth disease virus and which is capable of expressing said structural proteins and 3C proteinase in animals susceptible to foot and mouth disease, wherein said structural proteins stimulate an immune response when administered to said animals, wherein said interferon-α and/or interferor-β protein is expressed prior to development of specific immunity to said structural proteins and 3C proteinase, wherein said expressed interferon-α and/or interferon-β protein results in an early-acting anti-FMDV effect, inhibiting or delaying onset or severity of said foot and mouth disease when said animals are challenged with virulent FMDV within one to seven days post administration, and wherein said expression of said construct which encodes all the viral structural proteins and the 3C proteinase of a FMDV stimulates a protective long term immune response in said animals.

11. A method for protecting susceptible animals from foot and mouth disease comprising:
administering to said animals an effective dosage of an anti-FMDV vaccine, said vaccine comprising an effective amount of: a single viral gene transfer vector wherein said vector is an adenovirus and wherein said vector comprises a first nucleic acid construct capable of expressing an interferon-α protein of cloven-hooved animal origin and/or an interferon-β protein of porcine origin in animals susceptible to foot and mouth disease, and a second nucleic acid construct which encodes all the viral structural proteins and the 3C proteinase of a foot and mouth disease virus and which is capable of expressing said structural proteins and 3C proteinase in animals susceptible to foot and mouth disease, wherein said structural proteins stimulate an immune response when administered to said animals, wherein said interferon-α and/or interferon-β protein is expressed prior to development of specific immunity to said structural proteins and 3C proteinase, wherein said expressed interferon-α and/or interferon-β protein results in an early-acting anti-FMDV effect, inhibiting or delaying onset or severity of said foot and mouth disease when said animals are challenged with virulent FMDV within one to seven days post administration, and wherein said expression of said construct which encodes all the viral structural proteins and the 3C proteinase of a FMDV stimulates a protective long term immune response in said animals.

12. The method of claim 10 or 11 wherein said animals susceptible to foot and mouth disease are swine, cattle, or sheep.

13. A method of inducing an early-acting anti-FMDV effect to protect susceptible animals from foot and mouth disease comprising:
administering to said animals an effective dosage of a vaccine comprising an adenovirus vector, wherein said vector comprises an effective amount of a nucleic acid construct capable of expressing an interferon-α protein of cloven-hooved animal origin and/or an interferon-β protein of porcine origin in animals susceptible to foot and mouth disease and wherein said administration is effective for inhibiting or delaying onset or severity of said foot and mouth disease when said animals are challenged with virulent FMDV within one to seven days post administration.

14. The method of claim 13 wherein said animals susceptible to foot and mouth disease are swine, cattle, or sheep.

15. An early-acting effective anti-foot and mouth disease virus vaccine suitable for administering intramuscularly to animals, said vaccine comprising an effective amount of a single nucleic acid construct which is a DNA sequence which is capable of expressing an interferon-α protein of cloven-hooved animal origin and/or an interferon-β protein of porcine origin and all the viral structural proteins and the 3C proteinase of a foot and mouth disease virus (FMDV) in animals susceptible to foot and mouth disease, wherein said structural proteins stimulate an immune response when administered to said animals, and wherein said interferon-α and/or interferon-β protein is expressed prior to development of specific immunity to said structural proteins and 3C proteinase.

16. A method for protecting susceptible bovine animals from foot and mouth disease comprising:

administering to said animals an effective dosage of an anti-FMDV vaccine, said vaccine comprising an effective amount of: a viral gene transfer vector wherein said vector is an adenovirus and wherein said vector comprises a nucleic acid construct capable of expressing an interferon-β protein of bovine origin in bovine animals susceptible to foot and mouth disease, and (2) an effective FMDV vaccine in an amount effective for stimulating an immune response when administered to said animals, wherein said bovine interferon-β protein is expressed prior to development of specific immunity to said effective FMDV vaccine, wherein said expressed bovine interferon-β protein results in an early-acting antiviral effect, inhibiting or delaying onset or severity of said foot and mouth disease when challenged with virulent FMDV within one to seven days post administration, and wherein said effective FMDV vaccine stimulates a protective long term immune response in said animals.

17. A method for protecting susceptible bovine animals from foot and mouth disease comprising:
administering to said animals an effective dosage of an anti-FMDV vaccine, said vaccine comprising an effective amount of: a first-viral gene transfer vector wherein said first vector is an adenovirus and wherein said first vector comprises a nucleic acid construct capable of expressing an interferon-β protein of bovine origin in bovine animals susceptible to foot and mouth disease, and a second viral gene transfer vector wherein said second vector is an adenovirus and wherein said second vector comprises a nucleic acid construct which encodes all the viral structural proteins and the 3C proteinase of a foot and mouth disease virus and which is capable of expressing said structural proteins and 3C proteinase in bovine animals susceptible to foot and mouth disease, wherein said structural proteins stimulate an immune response when administered to said bovine animals, wherein said bovine interferon-β protein is expressed prior to development of specific immunity to said structural proteins and 3C proteinase, wherein said expressed bovine interferon-β protein results in an early-acting anti-FMDV effect, inhibiting or delaying onset or severity of said foot and mouth disease when said bovine animals are challenged with virulent FMDV within one to seven days post administration, and wherein said expression of said construct which encodes all the viral structural proteins and the 3C proteinase of a FMDV stimulates a protective long term immune response in said animals.

18. A method for protecting susceptible bovine animals from foot and mouth disease comprising:
administering to said animals an effective dosage of an anti-FMDV vaccine, said vaccine comprising an effective amount of: a single viral gene transfer vector wherein said vector is an adenovirus and wherein said vector comprises a first nucleic acid construct capable of expressing an interferon-β protein of bovine origin in animals susceptible to foot and mouth disease, and a second nucleic acid construct which encodes all the viral structural proteins and the 3C proteinase of a foot and mouth disease virus and which is capable of expressing said structural proteins and 3C proteinase in animals susceptible to foot and mouth disease, wherein said structural proteins stimulate an immune response when administered to said animals, wherein said bovine interferon-β protein is expressed prior to development of specific immunity to said structural proteins and 3C proteinase, wherein said expressed bovine interferon-β protein results in an early-acting anti-FMDV effect, inhibiting or delaying onset or severity of said foot and mouth disease when said bovine animals are challenged with virulent FMDV within one to seven days post administration, and wherein said expression of said construct which encodes all the viral structural proteins and the 3C proteinase of a FMDV stimulates a protective long term immune response in said animals.

19. A method of inducing an early-acting anti-FMDV effect to protect susceptible bovine animals from foot and mouth disease comprising:
administering to said animals an effective dosage of a vaccine comprising an adenovirus vector, wherein said vector comprises an effective amount of a nucleic acid construct capable of expressing an interferon-β protein of bovine origin in bovine animals susceptible to foot and mouth disease and wherein said administration is effective for inhibiting or delaying onset or severity of said foot and mouth disease when said bovine animals are challenged with virulent FMDV within one to seven days post administration.

* * * * *